US 6,211,170 B1

(12) United States Patent
Yoakim et al.

(10) Patent No.: US 6,211,170 B1
(45) Date of Patent: Apr. 3, 2001

(54) AZETIDINONE DERIVATIVES FOR THE TREATMENT OF HCMV INFECTIONS

(75) Inventors: Christiane Yoakim, Laval; Robert Déziel, Mont-Royal; Stephen Kawai, Côte St-Luc; William W. Ogilvie, Rosemère; Jeffrey O'Meara, Laval; Catherine Chabot, Terrebonne, all of (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 09/167,141

(22) Filed: Oct. 6, 1998

Related U.S. Application Data
(60) Provisional application No. 60/061,548, filed on Oct. 7, 1997.

(51) Int. Cl.[7] .............. C07D 205/08; A61K 31/397; A61K 31/522; A61K 31/52; A61P 31/22
(52) U.S. Cl. .............. 514/210.02; 540/200; 514/261; 514/262
(58) Field of Search .............. 514/210, 261, 514/262; 540/200

(56) References Cited

U.S. PATENT DOCUMENTS

| 5,100,880 | 3/1992 | Durette et al. . |
| 5,104,862 | 4/1992 | Durette et al. . |
| 5,229,381 | 7/1993 | Doherty et al. . |

FOREIGN PATENT DOCUMENTS

| 0199630 | 10/1986 | (EP) . |
| 0377549 | 10/1989 | (EP) . |
| 2266527 | 11/1993 | (GB) . |
| WO 95/02579 | 1/1995 | (WO) . |

OTHER PUBLICATIONS

Hagmann et al., Bioog. Med. Chem. Lett, 1992, vol. 2, p. 681.
Hagmann et al., J. Med. Chem. 1993, vol. 36, p. 771.
Shah et al., Bioorg. Med. Chem. Lett. 1993, vol. 3, p. 2295.
Finke et al., J. Med. Chem. 1995, vol. 38, p. 2449.

Kobayashi et al., Chemical Abstracts, vol. 124, Abs. 29520, 1996 for Japanese Patent Application 07242624 published Sep. 19, 1995 (Nippon Tabacco).
Boeheme et al., Annual Reports in Medicinal Chemistry, 1995, vol. 30, p. 139.

*Primary Examiner*—Mark L. Berch
(74) *Attorney, Agent, or Firm*—Robert P. Raymond; Alan R. Stempel; Mary-Ellen M. Devlin

(57) ABSTRACT

A compound of formula I:

(I)

wherein $R_1$ is hydrogen, methyl, ethyl, methoxy or methylthio; $R_2$ and $R_3$ each independently is hydrogen or $C_{1-3}$ alkyl; $R_4$ is hydrogen, lower alkyl, methoxy, ethoxy, or benzyloxy; $R_5$ is lower alkyl, lower cycloalkyl, $(CH_2)_mC(O)OR_6$ wherein m is the integer 1 or 2 and $R_6$ is lower alkyl, phenyl optionally substituted with $C(O)OR_7$ wherein $R_7$ is lower alkyl or phenyl (lower alkyl); or $R_6$ is Het or Het (lower alkyl); or $R_4$ and $R_5$ together with the nitrogen atom to which they are attached form a nitrogen containing ring optionally substituted with benzyloxycarbonyl or with phenyl optionally substituted among other group with $C(O)OR_7$ wherein $R_7$ is lower alkyl or (lower alkyl)phenyl; X is selected from the group consisting of O, S, SO, $SO_2$, $NR_8$, wherein $R_8$ is H or lower alkyl; and Y is $C_{1-10}$ non-cyclic or cyclic alkyl; $[(CH_2)_{0-1}]$-phenyl, said phenyl ring optionally substituted; Het or Het(lower alkyl); or when X is $NR_8$, wherein $R_8$ is lower alkyl and Y is lower alkyl or lower alkoxy, X and Y are joined together to form a morpholino or piperidino ring;

or a therapeutically acceptable acid addition salt thereof, which compound is useful in the treatment of HCMV infection.

9 Claims, No Drawings

AZETIDINONE DERIVATIVES FOR THE TREATMENT OF HCMV INFECTIONS

This application claims the benefit under 35 U.S.C. § 119 (e) of U.S. Provisional Application Ser. No. 60/061,548, filed Oct. 7, 1997.

FIELD OF THE INVENTION

This invention relates to azetidinone derivatives having activity against herpes infections. More specifically, the invention relates to azetidin-2-one derivatives exhibiting antiherpes activity, to pharmaceutical compositions comprising the derivatives, and methods of using the derivatives to inhibit the replication of herpes virus and to treat herpes infections.

BACKGROUND OF THE INVENTION

Herpes viruses inflict a wide range of diseases against humans and animals. For instance, herpes simplex viruses, types 1 and 2 (HSV-1 and HSV-2), are responsible for cold sores and genital lesions, respectively; varicella zoster virus (VZV) causes chicken pox and shingles; and the human cytomegalovirus (HCMV) is a leading cause of opportunistic infections in immunosuppressed individuals.

Over the past two decades, a class of compounds known as the purine and pyrimidine nucleoside analogs has received the most attention by investigators in the search for new therapeutic agents for treatment of infections. Another nucleoside analog, ganciclovir, has been used with some success in treating HCMV infections.

Nevertheless, in spite of some significant advances, the need for effective, safe therapeutic agents for treating herpes viral infections continues to exist. For a review of current therapeutic agents in this area, see R. E. Boeheme et al., Annual Reports in Medicinal Chemistry, 1995, 30, 139.

Azetidin-2-one derivatives have been reported in the literature as having variety of biological activities; mainly antibacterial, antiinflammatory, antidegenerative, etc. However, azetidin-2-one derivatives have not been reported to be antiviral agents against herpes viruses.

The following references disclose azetidin-2-ones having biological activity:

S. K. Shah et al., European patent application 0,199,630, Oct. 29, 1986,
S. K. Shah et al., European patent application 0,377,549, Oct. 18, 1989,
P. L. Durette and M. Maccoss, U.S. Pat. No. 5,100,880, Mar. 31, 1992,
P. L. Durette and M. Maccoss, U.S. Pat. No. 5,104,862, Apr. 14, 1992,
W. K. Hagmann et al., Bioorg. Med. Chem. Lett. 1992, 2, 681,
W. K. Hagmann et al., J. Med. Chem. 1993, 36, 771,
J. B. Doherty et al., U.S. Pat. No. 5,229,381, issued Jul. 20, 1993,
S. K. Shah et al., Bioorg. Med. Chem. Lett. 1993, 3, 2295,
G. Crawley, PCT patent WO 95/02579, published Jan. 26, 1995,
P. E. Finke et al., J. Med. Chem. 1995, 38, 2449, and K. Kobayashi et al., Japanese patent application 07242624, published Sep. 19, 1995; Chem. Abstr. 1996, 124, 29520.

SUMMARY OF THE INVENTION

The present application discloses a group of azetidin-2-one derivatives particularly active against cytomegalovirus. This activity coupled with a wide margin of safety, renders these derivatives desirable agents for combating herpes infections.

The present azetidin-2-one derivatives are distinguished from the prior art compounds in that they possess different chemical structures and biological activities.

The azetidin-2-one derivatives are represented by formula 1:

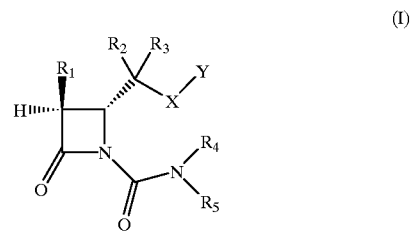

wherein $R_1$ is hydrogen, methyl, ethyl, methoxy or methylthio;
$R_2$ and $R_3$ each independently is hydrogen or $C_{1-3}$ alkyl;
$R_4$ is hydrogen, lower alkyl, methoxy, ethoxy, or benzyloxy;
$R_5$ is lower alkyl, lower cycloalkyl, $(CH_2)_m C(O)OR_6$
  wherein m is the integer 1 or 2 and $R_6$ is lower alkyl or phenyl(lower alkyl);
phenyl, phenyl monosubstituted, disubstituted or trisubstituted with a substituent selected independently from the group consisting of lower alkyl, lower alkoxy, lower alkylthio, halo, hydroxy and amino; phenyl(lower alkyl), phenyl(lower alkyl) monosubstituted or disubstituted on the phenyl portion thereof with a substituent selected independently from the group consisting of lower alkyl, lower alkoxy, lower alkylthio, halo, hydroxy, nitro, amino, lower alkylamino, di(lower alkyl)amino, lower acylamino, di(lower alkyl)aminocarbonyl, cyano, trifluoromethyl, (trifluoromethyl)thio, (trifluoromethyl)sulfinyl, (trifluoromethyl)sulfonyl
  and $C(O)OR_7$ wherein $R_7$ is lower alkyl or phenyl(lower alkyl);
Het or Het(lower alkyl) wherein Het represents an unsubstituted, monosubstituted or disubstituted five or six membered, monovalent heterocyclic ring containing one or two heteroatoms selected from the group consisting of N, O or S, wherein each substituent is selected independently from the group consisting of lower alkyl, lower alkoxy, halo and hydroxy;
5-(benzo[1,3]dioxolyl)methyl, (1(R)-1-naphthalenyl)ethyl, 2-benzothiazolyl or 2-thiazolo[4,5-b]pyridinyl; or
$R_4$ and $R_5$ together with the nitrogen atom to which they are attached form a piperidino, morpholino, thiomorpholino, piperazino, N-methylpiperazino, 1-(3,4-dihydro-1H-isoquinolinyl) or 2-(3,4-dihydro-1H-isoquinolinyl) or a pyrrolidino ring optionally substituted with benzyloxycarbonyl or with phenyl, said phenyl ring optionally mono- or di-substituted with a substituent selected independently from the group consisting of lower alkyl, lower alkoxy, lower alkylthio, halo, hydroxy, nitro, amino, lower alkylamino, di(lower alkyl)amino, lower acylamino, di(lower alkyl)aminocarbonyl, cyano, trifluoromethyl, (trifluoromethyl)thio, (trifluoromethyl)sulfinyl, (trifluoromethyl)sulfonyl and $C(O)OR_7$ wherein $R_7$ is as defined above;
X is selected from the group consisting of O, S, SO, $SO_2$, $NR_8$, wherein $R_8$ is H or lower alkyl; and
Y is $C_{1-10}$ non-cyclic or cyclic alkyl; phenyl(lower alkyl), said phenyl ring optionally mono- or di-substituted with a lower alkyl or lower alkoxy, said phenyl ring being optionally fused with an aromatic ring to form a bicyclic ring, said aromatic ring optionally containing a heteroatom selected from the group consisting of N, O and S; Het or Het(lower alkyl) containing one or more heteroatom selected from the group consisting of N, O, and S, said Het optionally mono- or di-substituted with a lower alkyl or lower alkoxy group; said heterocyclic ring being optionally fused with an aromatic ring to form a bicyclic ring, said aromatic ring optionally containing one or more heteroatom selected from the group consisting of N, O and S; $C(O)R_9$ wherein $R_9$ is lower alkyl or phenyl(lower alkyl);

or when X is $NR_8$, wherein $R_8$ is lower alkyl and Y is lower alkyl or lower alkoxy, X and Y are joined together to form a morpholino or piperidino ring;

or a therapeutically acceptable acid addition salt thereof.

Preferred compounds of the invention include compounds of formula (1) wherein $R_1$ is hydrogen or $C_{1-2}$ alkyl;

$R_2$ and $R_3$ each independently is hydrogen, methyl or ethyl;

$R_4$ is hydrogen or lower alkyl;

$R_5$ is phenyl optionally substituted with a substituent selected independently from the group consisting of lower alkyl, lower alkoxy; phenyl(lower alkyl) optionally mono- or di-substituted on the phenyl portion thereof with a substituent selected independently from the group consisting of lower alkyl, lower alkoxy, nitro, halo, cyano, trifluoromethyl, and $C(O)OR_7$ wherein $R_7$ is lower alkyl or phenyl(lower alkyl);

Het(lower alkyl) wherein Het represents a five or six-membered, monovalent heterocyclic ring containing a heteroatom selected from the group consisting of N, O, or S, said ring being optionally substituted with lower alkyl or lower alkoxy;

or $R_4$ and $R_5$ together with the nitrogen atom to which they are attached form a pyrrolidino optionally substituted with benzyloxycarbonyl or phenyl said phenyl ring optionally mono- or di-substituted with halo, nitro, cyano or trifluoromethyl;

X is selected from the group consisting of O, S, $NR_8$, wherein $R_8$ is H or lower alkyl; and Y is $C_{1-10}$ non-cyclic or cyclic alkyl; phenylcarbonyl; phenyl or benzyl optionally mono- or di-substituted with lower alkyl or lower alkoxy, said phenyl ring being optionally fused with an aromatic ring to form a bicyclic ring, said aromatic ring optionally containing a heteroatom selected from the group consisting of N, O and S; and Het or $CH_2$-Het containing one or more heteroatom selected from the group consisting of N, O, and S, said Het optionally mono- or di-substituted with a lower alkyl or lower alkoxy group; said heterocyclic ring being optionally fused with an aromatic ring to form a bicyclic ring, said aromatic ring optionally containing one or more heteroatom selected from the group consisting of N, O and S;

or when X is $NR_8$, wherein $R_8$ is lower alkyl and Y is lower alkyl, X and Y are joined together to form a piperidino ring.

More preferred compounds of the invention include compounds of formula 1 wherein $R_1$, $R_2$ and $R_3$ each independently is hydrogen, methyl or ethyl;

$R_4$ is hydrogen or $C_{1-3}$ alkyl;

$R_5$ is phenyl optionally substituted with a substituent selected independently from the group consisting of lower alkyl or lower alkoxy; ($C_{1-2}$ alkyl)phenyl optionally mono- or di-substituted on the phenyl portion thereof with a substituent selected independently from the group consisting of lower alkyl, lower alkoxy, nitro, halo, cyano, trifluoromethyl, and $C(O)OR_7$ wherein $R_7$ is lower alkyl or (lower alkyl)phenyl;

X is selected from the group consisting of O, S, $NR_8$, wherein $R_8$ is H or lower alkyl; and Y is lower non-cyclic or cyclic alkyl; phenyl optionally mono- or di-substituted with lower alkyl or lower alkoxy; or Het containing one or more heteroatom selected from the group consisting of N, O, and S, said Het optionally mono- or di-substituted with a lower alkyl; said heterocyclic ring being optionally fused with an aromatic ring to form a bicyclic ring, said aromatic ring optionally incorporating one or more heteroatom selected from the group consisting of N, O and S;

or when X is $NR_8$, wherein $R_8$ is lower alkyl and Y is lower alkyl, X and Y are joined together to form a piperidino ring.

Most preferred compounds of the invention include compounds of formula (1) wherein $R_1$, $R_2$ and $R_3$ each independently is hydrogen;

$R_4$ is hydrogen or methyl;

$R_5$ is benzyl optionally mono-substituted on the phenyl portion thereof with nitro or trifluromethyl, or 1(R)-phenylethyl;

X is S; and

Y is pyrimidine optionally substituted with lower alkyl; pyridine; N-Me-tetrazole; or benzoxazole.

Included within the scope of this invention is a pharmaceutical composition for treating cytomegalovirus infections in a human comprising a compound of formula 1, or a therapeutically acceptable salt thereof, and a pharmaceutically acceptable carrier.

The scope of the invention also includes a method for treating cytomegalovirus infections in a human comprising administering thereto an effective amount of the compound of formula 1, or a therapeutically acceptable salt thereof.

Also included within the scope is a method for protecting human cells against cytomegalovirus pathogenesis comprising treating said cells with an anti-cytomegalovirus effective amount of a compound of formula 1, or a therapeutically acceptable salt thereof.

Compounds of formula 1 according to the present invention may also be used in co-therapies, with other conventional anti-herpes compounds, such as but not limited to ganciclovir, foscarnet, acyclovir, valaciclovir, famciclovir, cidofovir, penciclovir and lobucavir.

Compounds of formula 1 according to the present invention may also be used in co-therapies with anti-retroviral compounds such as reverse transcriptase inhibitors (i.e. AZT, 3TC) or protease inhibitors.

Processes for preparing the compounds of formula 1 are described hereinafter.

DETAILED DESCRIPTION OF THE INVENTION

General

As used herein, the following definitions apply unless otherwise noted:

With reference to the instances where (R) or (S) is used to designate the configuration of a radical, e.g. $R_5$ of the compound of formula 1, the designation is done in the context of the compound and not in the context of the radical alone.

The term "residue" with reference to an amino acid or amino acid derivative means a radical derived from the corresponding α-amino acid by eliminating the hydroxyl of the carboxy group and one hydrogen of the α-amino group.

For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid derivative means a residue attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The term "halo" as used herein means a halo radical selected from bromo, chloro, fluoro or iodo.

The term "lower alkyl" or (lower alkyl) as used herein, either alone or in combination with another radical, means straight or branched chain alkyl radicals containing up to six carbon atoms and includes methyl, ethyl, propyl, butyl, hexyl, 1-methylethyl, 1-methylpropyl, 2-methylpropyl and 1,1-dimethylethyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "lower alkanoyl" as used herein, either alone or in combination with another radical, means a straight chain 1-oxoalkyl containing from one to six carbon atoms or a branched chain 1-oxoalkyl containing from four to six carbon atoms; for example, acetyl, propionyl (1-oxopropyl), 2-methylpropionyl and 2-ethylbutyryl.

The term "lower cycloalkyl" as used herein, either alone or in combination with another radical, means saturated cyclic hydrocarbon radicals containing from three to seven carbon atoms and includes cyclopropyl, cyclobutyl, cyclopentyl, cyclohexyl and cycloheptyl.

The term "amino" as used herein means an amino radical of formula —$NH_2$. The term "lower alkylamino" as used herein means alkylamino radicals containing one to six carbon atoms and includes methylamino, propylamino, (1-methylethyl)amino and (2-methylbutyl)amino. The term "di(lower alkyl)amino" means an amino radical having two lower alkyl substituents each of which contains one to six carbon atoms and includes dimethylamino, diethylamino, ethylmethylamino and the like.

The term "Het" as used herein means a monovalent radical derived by removal of a hydrogen from a five- or six-membered saturated or unsaturated heterocycle containing from one to four heteroatoms selected from nitrogen, oxygen and sulfur. Optionally, the heterocycle may bear one or two substituents; for example, N-oxido, lower alkyl, ($C_{1-3}$)alkylphenyl, lower alkoxy, halo, amino or lower alkylamino. Again optionally, the five- or six-membered heterocycle can be fused to a phenyl. Examples of suitable heterocycles and optionally substituted heterocycles include pyrrolidine, tetrahydrofuran, thiazolidine, pyrrole, 1H-imidazole, 1-methyl-1H-imidazole, pyrazole, furan, thiophene, oxazole, isoxazole, thiazole, 2-methylthiazole, 2-aminothiazole, 2-(methylamino)-thiazole, piperidine, 1-methylpiperidine, 1-methylpiperazine, 1,4-dioxane, morpholine, pyridine, pyridine N-oxide, pyrimidine, 2,4-dihydroxypyrimidine, 2,4-dimethylpyrimidine, 2,6-dimethylpyridine, 1-methyl-1H-tetrazole, 2-methyl-2H-tetrazole, benzothiazole, benzoxazole and thiazolo[4,5-b]-pyridine.

The term "pharmaceutically acceptable carrier" as used herein means a non-toxic, generally inert vehicle for the active ingredient which does not adversely affect the ingredient.

The term "effective amount" means a predetermined antiviral amount of the antiviral agent, i.e. an amount of the agent sufficient to be effective against the virus in vivo.

The azetidin-2-one derivatives of formula 1 can be obtained in the form of therapeutically acceptable acid addition salts. In the instance where a particular derivative has a residue which functions as a base, examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and salts with inorganic acids such as hydrohalic acids, e.g. hydrochloric acid, or sulfuric acid, or phosphoric acid.

Process

Compounds of formula 1 can be synthesized from commercially available, suitably protected amino acids, as exemplified hereinafter. (For general synthetic procedures see: *The Organic Chemistry of beta-Lactams,* Gunda I. Georg, Ed.; VCH Publishers Inc., New York, N.Y., USA, 1992, pp 1 to 48 and 257 to 293.)

Compounds of formula 1 wherein $R_1$ to $R_5$ inclusive, X and Y are as defined in the summary of the invention, can be prepared by the following generic process illustrated in scheme A:

scheme A

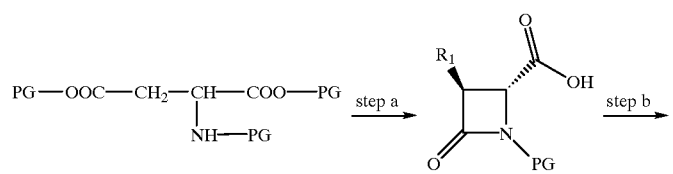

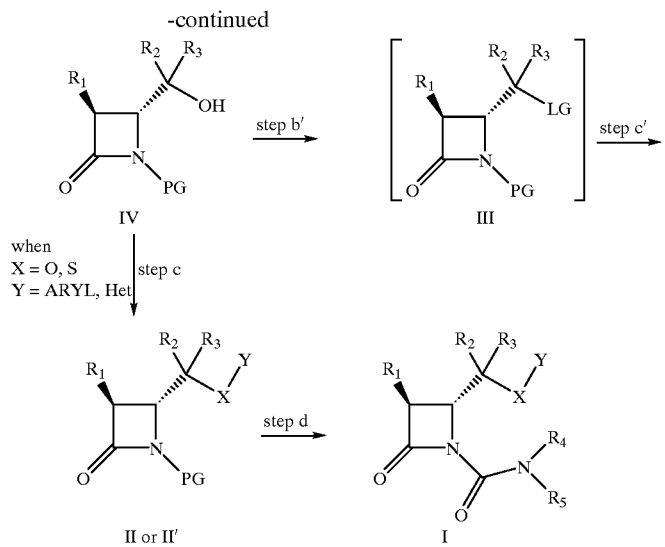

Step a: Intermediate V is prepared according to known procedures starting from suitably protected D-aspartic acid (ref. P. E. Finke et al., J. Med. Chem. 1995, 38, 2449).

Step b: The acid function of intermediate V is reduced to give alcohol IV.

Step c: When X is O or S, and Y is aryl or Het, the primary alcohol IV is converted into intermediate II, using Mitsunobu reaction conditions (Ref. D. L. Hughes, Org. Reaction 1992, 42, 335; J. R. Dormoy, Synthesis 1982, 753).

Alternatively, when X and Y are as defined in the summary of the invention, the process is carried out by an alternate route using steps b' and c':

Step b': The alcohol IV is converted into a leaving group "LG" (e.g. mesylate, iodide, bromide) to give intermediate III.

Step c': The intermediate III is then reacted with a nucleophile (e.g. alkylthiolate or amine) to yield an alternative key intermediate II'.

Step d: Key intermediates II or II' are converted to the desired inhibitor via deprotection using fluoride ions (e.g. cesium fluoride), followed by condensation with the appropriate reagent.

In the case of compounds of formula 1 wherein $R_4$ is hydrogen, the appropriate reagent is an isocyanate of formula $R_5'$—NCO, wherein $R_5'$ is as defined above but not pyridine, and the condensation is done in the presence of a tertiary amine (e.g. diisopropylethylamine) or preferably lithium bis(trimethylsilyl) amide.

Alternatively, in the case of compounds of formula 1 wherein $R_4$ is a lower alkyl, then the appropriate reagent is an activated carbamate of formula VI:

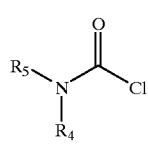

and the condensation is done in the presence of a base such as lithium bis(trimethylsilyl) amide.

Still, as a further alternative to the general process of scheme A, compounds of formula 1 wherein $R_5$ is pyridine can be produced by the condensation of an intermediate of formula II or II' with an activated carbamate of formula VI':

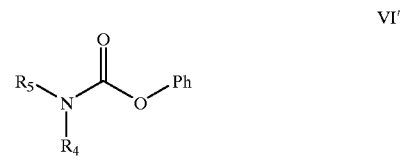

Furthermore, the activated carbamate of formula VI or VI' can be used in the condensation of intermediate II or II' when the appropriate isocyanate $R_5'$—NCO is not available commercially.

To further illustrate the process according to the invention, there are provided specific examples of the alternative processes described in scheme A.

Scheme B

As a first alternative, there is provided a process where compounds of formula 1 (wherein $R_1$, $R_4$ and $R_5$ are as defined above and $R_2$ and $R_3$ are both H, X is O or S, and Y is phenyl or Het) were prepared as illustrated in scheme B:

Scheme B

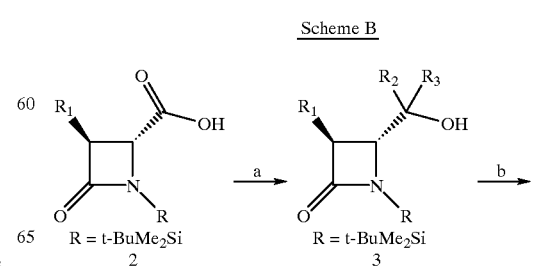

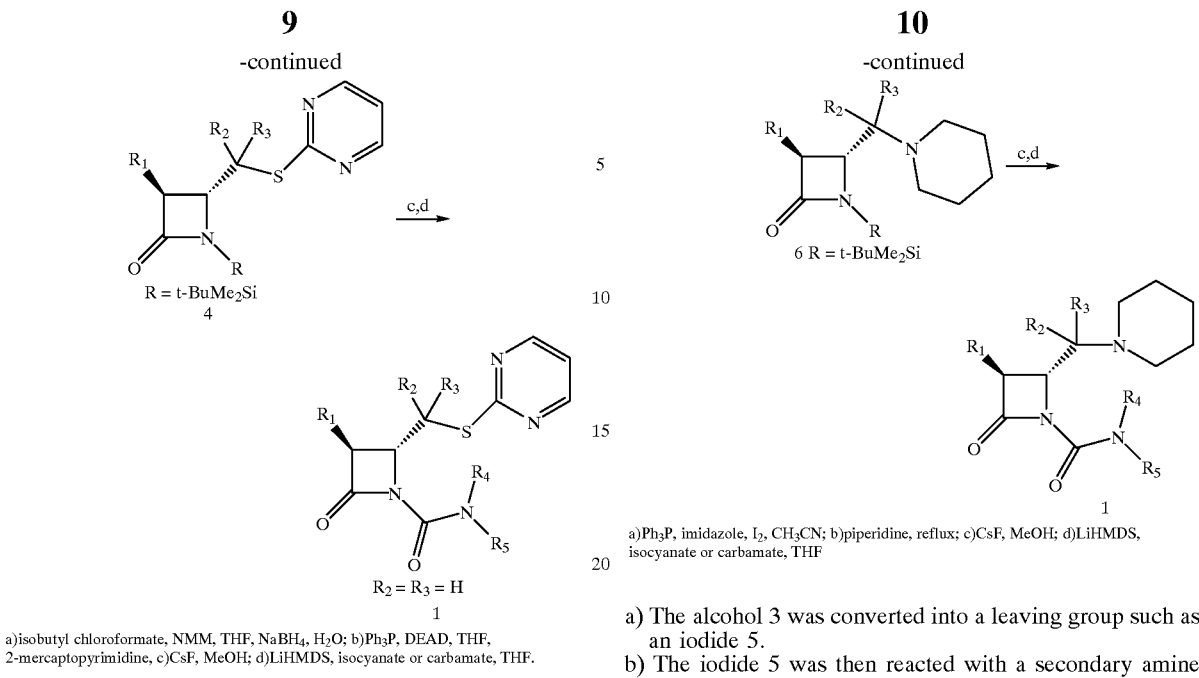

a)isobutyl chloroformate, NMM, THF, NaBH$_4$, H$_2$O; b)Ph$_3$P, DEAD, THF, 2-mercaptopyrimidine, c)CsF, MeOH; d)LiHMDS, isocyanate or carbamate, THF.

a) Reduction of acid 2 was achieved with borane in tetrahydrofuran or via the formation of a mixed anhydride with isobutylchloroformate in the presence of an organic tertiary amine e.g. N-methylmorpholine or diisopropylethylamine, and subsequent treatment of the mixed anhydride with sodium borohydride.

b) Conversion of the alcohol 3 into arylether or arylthioether 4 was achieved using Mitsunobu reaction conditions (Ref. D. L. Hughes, Org. Reaction 1992, 42, 335; J. R. Dormoy, Synthesis 1982, 753) for example using triphenylphosphine and diethyl azodicarboxylate in a solvent such as tetrahydrofuran and in the presence of an arylthiol or arylalcohol.

c, d) Intermediate 4 was converted to the desired inhibitor 1 via deprotection using a source of fluoride ions such as cesium fluoride, followed by condensation with the appropriate isocyanate R$_5$—NCO in the presence of a tertiary amine such as diisopropylethylamine or preferably lithium (or potassium) bis(trimethylsilyl)amide [when R$_4$ is H]. Alternatively, an activated carbamate such as phenoxycarbamate could be used. When R$_4$ is not hydrogen, an appropriate carbamoyl chloride derivative should be used.

Scheme C

Alternatively, the compounds of formula 1 wherein R$_1$ to R$_5$ inclusive are as defined above, X is NR$_8$ (wherein R$_8$ is defined as in the summary of the invention) or X and Y are joined to form a morpholino or piperidino ring, were prepared by the process as illustrated in scheme C:

Scheme C

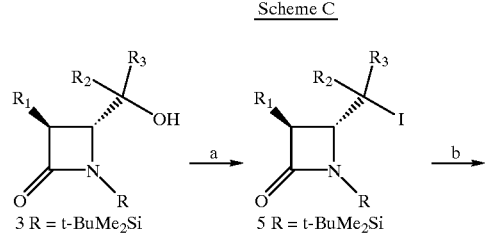

a)Ph$_3$P, imidazole, I$_2$, CH$_3$CN; b)piperidine, reflux; c)CsF, MeOH; d)LiHMDS, isocyanate or carbamate, THF a) The alcohol 3 was converted into a leaving group such as an iodide 5.
b) The iodide 5 was then reacted with a secondary amine such as piperidine or morpholine to give 6 wherein X and Y are joined to form a piperidino or morpholino ring respectively.
c) The intermediate 6 was then elaborated as described above to yield a compound of formula 1.
d)

Scheme D

Turning now to a further specific embodiment of the process of the invention, there is provided a process for producing compounds of formula 1 wherein R$_2$ is C$_{1-3}$ alkyl such as methyl, Y is phenyl or Het, R$_3$ is H, and R$_1$, R$_4$, R$_5$, and X are as defined in the summary of the invention. These compounds were prepared by the process as illustrated in scheme D:

Scheme D

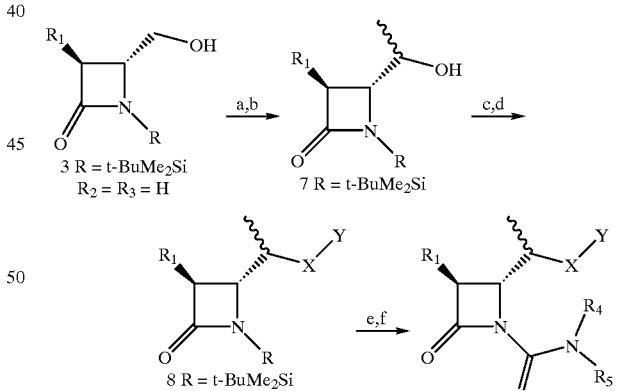

a)oxalyl chloride, DMSO, CH$_2$Cl$_2$; b)MeMgBr, THF; c)Ph$_3$P, DEAD, THF, 2-mercaptopyrimidine, d)separation of diastereoisomers; e)CsF, MeOH; f)LiHMDS, isocyanate or carbamate, THF.

a, b) The primary alcohol 3 was oxidized to the corresponding aldehyde using oxalyl chloride-activated dimethyl sulfoxide (K. Omura and D. Swern, Tetrahedron 1978, 34, 1651) or triacetoxy periodinane (D. B. Dess and J. C. Martin, J. Org. Chem. 1983, 48, 4155). This aldehyde was then reacted with an appropriate Grignard reagent such as methylmagnesium bromide to give the addition product 7 as a mixture of diastereoisomers.

c, d) Conversion of the secondary alcohols 7 into arylether or arylthioether 8 was achieved using Mitsunobu reaction conditions as exemplified in Scheme B, step b. The two diastereoisomers could then be separated using chromatography on silica gel or by preparative HPLC.

e, f) The desired inhibitor 1 was obtained via deprotection and condensation as described above.

Schemes E, F, G, and H

Isocyanates or activated carbamates used in this invention which were not commercially available, were prepared as described in schemes E, F, G or H.

Scheme E: Isocyanates such as 1(R)-phenylpropyl isocyanate 10 were prepared from commercially available amine via the formation of the hydrochloride salt and reaction with triphosgene in toluene under reflux.

Scheme E

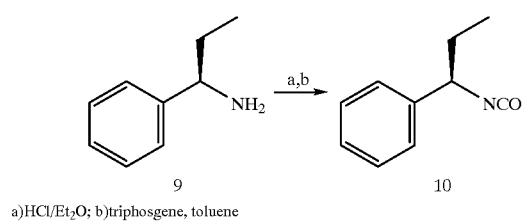

a)HCl/Et$_2$O; b)triphosgene, toluene

Scheme F: Alternatively, non commercially available secondary benzylic amines could be prepared from the corresponding substituted benzyl bromides as follows:

a) Benzylic bromide 11 was reacted with methylamine in ethanol to afford the corresponding secondary amine 12 which was isolated as the hydrochloride salt.

b) Further reaction with phosgene in presence of a tertiary organic base such as diisopropylethylamine in dichloromethane gave the desired carbamoyl chloride 13.

Scheme F

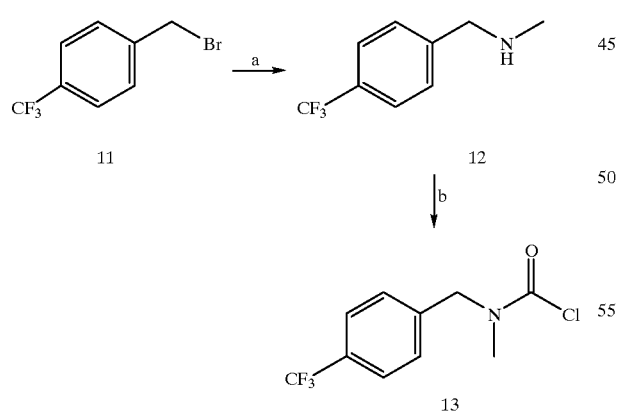

a)MeNH$_2$, EtOH, HCl/Et$_2$O; b)phosgene, DIEA, CH$_2$Cl$_2$

Scheme G: Alternatively, preactivation could be achieved via formation of the N-phenoxycarbamate derivative 15 by reacting the amine 14 with phenyl chloroformate in the presence of a tertiary amine such as triethylamine in dichloromethane.

Scheme G

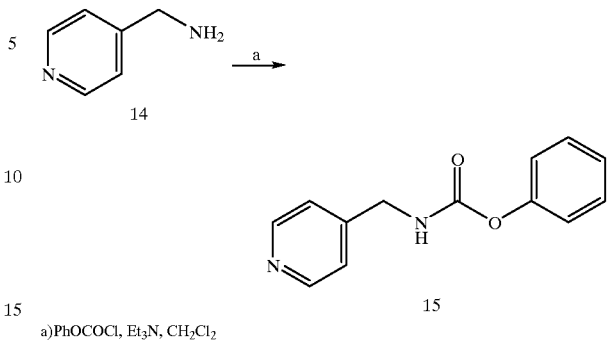

a)PhOCOCl, Et$_3$N, CH$_2$Cl$_2$

Scheme H: Alternatively, non commercially available pyrrolidine derivatives such as 19 could be prepared as follows:

a, b) Amine 16 was protected by reaction with di-tert-butylcarbonate in the presence of an aqueous base such as sodium hydroxide. The protected amine was reacted a benzyl halide such as benzyl bromide or chloride in presence of a base such as sodium hydride in tetrahydrofuran to give intermediate 17.

c) Cyclisation of intermediate 17 was accomplished using strong base such as n-butyllithium in the presence of tetramethylethylenediamine in tetrahydrofuran to give pyrrolidine derivative 18.

d, e) Cleavage of the tert-butyloxycarbonyl group is carried out under anhydrous acidic conditions followed by reaction with phosgene in presence of a tertiary organic base such as diisopropylethylamine in dichloromethane to give the desired carbamoyl chloride 19.

Scheme H

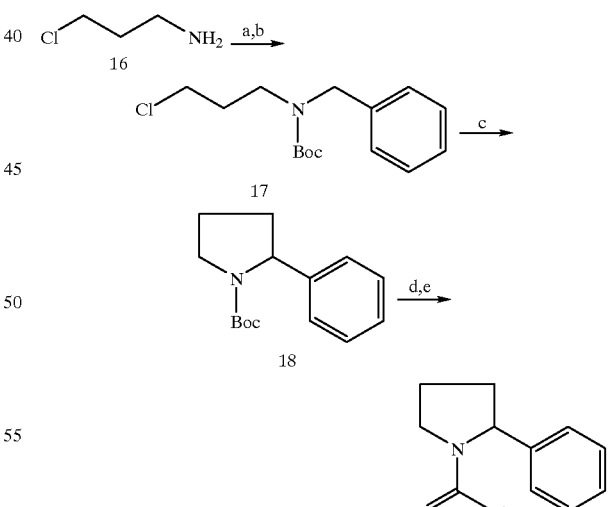

a)Boc$_2$O, THF, NaOH; b)NaH, THF, BnBr; c)n-BuLi, TMEDA,THF; d)HCl/dioxane; e)phosgene, DIEA, CH$_2$Cl$_2$ Scheme I Sulfoxides and sulfones are readily accessible from thioether intermediates such as 20, by using peroxide oxidation or preferably by reaction with oxone in a mixture of methanol/water as shown.

Scheme I

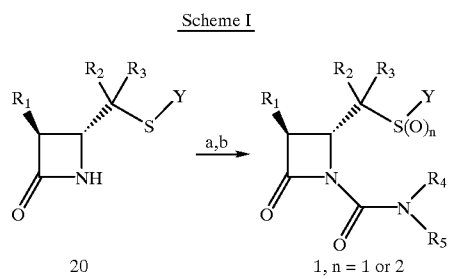

a) n=1, oxone (0.5 equiv.), MeOH, H₂O; n=2, oxone (1 equiv.), MeOH, H₂O,
b) LiHMDS, isocyanate or carbamate, THF Scheme J For compounds of formula 1 wherein Y is lower alkyl, introduction of a lower alkyl thioether could be achieved via intermediate 3.

a, b) The hydroxy group of the primary alcohol 3 was converted into a leaving group such as 4-nitrobenzenesulfonate, followed by displacement with potassium thioacetate to generate the corresponding thioacetate 21.

c, d) Saponification of the acetate 21 in the presence of lithium hydroxide in methanol followed by addition of methyl iodide gave the desired methylthioether derivative. Deprotection and ureido formation as described above led to the desired compound 1.

Scheme J

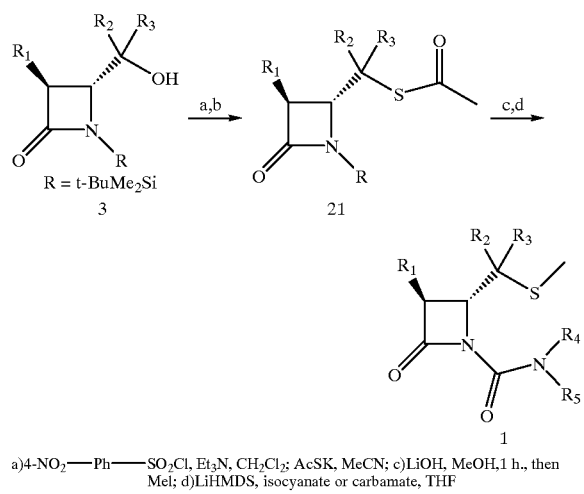

a) 4-NO₂—Ph—SO₂Cl, Et₃N, CH₂Cl₂; AcSK, MeCN; c) LiOH, MeOH,1 h., then MeI; d) LiHMDS, isocyanate or carbamate, THF Antiherpes Activity The antiherpes activity of the aforementioned azetidinone derivatives of formula 1 (HCMV protease inhibitors) can be demonstrated by biochemical, microbiological and biological procedures.

A biochemical procedure for demonstrating anticytomegalovirus activity for the azetidinone derivatives of formula 1 is described in the examples hereinafter. This particular assay determines the ability of a test compound to inhibit the activity ($IC_{50}$) of HCMV protease. More specifically, in the assay described herein, the inhibitory activity of the test compound is evaluated on the basis of its ability to interfere with the HCMV $N_O$ protease cleavage of a fluorogenic peptide substrate which in turn is based on the maturation cleavage site of the enzyme.

Methods for demonstrating the inhibiting effect of the azetidinone derivatives of formula 1 on CMV replication involving cell culture techniques ($EC_{50}$) are described in the examples herein.

When the HCMV protease inhibitor is employed as an antiviral agent, it is administered orally or systemically to humans in a vehicle comprising one or more pharmaceutically acceptable carriers, the proportion of which is determined by the solubility and chemical nature of the compound, chosen route of administration and standard biological practice. For oral administration, the compound or a therapeutically acceptable salt thereof can be formulated in unit dosage forms such as capsules or tablets each containing a predetermined amount of the active ingredient, ranging from about 50 to 500 mg, in a pharmaceutically acceptable carrier.

For parenteral administration, the HCMV protease inhibitor is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's, The Science and Practice of Pharmacy", 19$^{th}$ ed., Mack Publishing Company, Easton, Pa., 1995, or in "Pharmaceutical Dosage Forms and Drug Delivery Systems", 6$^{th}$ ed., H. C. Ansel et al., Eds., Williams & Wilkins, Baltimore, Md., 1995.

The dosage of the HCMV protease inhibitor will vary with the form of administration and the particular active agent chosen. Furthermore, it will vary with the particular host under treatment. Generally, treatment is initiated with small increments until the optimum effect under the circumstance is reached. In general, the inhibitor compound is most desirably administered at a concentration level that will generally afford antivirally effective results without causing any harmful or deleterious side effects.

For oral administration, the HCMV protease inhibitor is administered in the range of 20 to 200 mg per kilogram of body weight per day, with a preferred range of 25 to 100 mg per kilogram.

For ocular administration, the HCMV protease inhibitor is administered either topically or intraocularly (injection or implant) in a suitable preparation. For example, an implant containing the compound in a suitable formulation can be surgically implanted in the posterior segment of the eye through a small incision.

With reference to systemic administration, the HCMV protease inhibitor is administered at a dosage of 10 mg to 150 mg per kilogram of body weight per day, although the aforementioned variations will occur. However, a dosage level that is in the range of from about 10 mg to 100 mg per kilogram of body weight per day is most desirably employed in order to achieve effective results.

EXAMPLES

The following examples further illustrate this invention. All reactions were performed in a nitrogen or argon atmosphere. Temperatures are given in degrees Celsius. Solution percentages or ratios express a volume to volume relationship, unless stated otherwise. Nuclear magnetic resonance spectra were recorded on a Bruker 400 MHz spectrometer; the chemical shifts (δ) are reported in parts per million. Abbreviations or symbols used herein include: Boc: tert-butyloxycarbonyl; DEAD: diethyl azodicarboxylate; DIEA: diisopropylethylamine; DMF: dimethylformamide; Et: ethyl; EtOAc: ethyl acetate; Et$_2$O: diethyl ether; LiHMDS: lithium bis(trimethylsilyl)amide; Me: methyl; MeOH: methanol; MeCN: acetonitrile; Ph: phenyl; THF: tetrahydrofuran; TMEDA: tetramethylethylenediamine; MS(ES): electrospray mass spectrometry; MS(FAB): fast atom bombardment mass spectrometry; HRMS: high resolution mass spectrometry; PFU: plaque forming units.

Example 1
Preparation of 1(R)-phenylpropyl isocyanate

To a solution of 1(R)-phenylpropylamine (14.33 g, 106 mmol) in Et$_2$O (102 mL) was added a 1.0 M solution of HCl/Et$_2$O (212 mL, 212 mmol). The mixture was stirred for 30 min, then the crude solution was evaporated to dryness on a rotary evaporator. The resulting white hydrochloride salt was suspended in toluene (200 mL), triphosgene was added (11.67 g, 39.3 mmol) and the resulting suspension was stirred at reflux for 3 h at room temperature overnight. The reaction mixture was concentrated and the final volume adjusted to 200 mL with toluene giving a final concentration of 0.53M. The resulting isocyanate solution was used as such. An aliquot (170 mL) was concentrated to give a colorless oil.

$^1$H NMR (400 MHz, CDCl$_3$) δ 7.36–7.22 (m, 5H), 4.50 (t, J=6.7 Hz, 1H), 1.82 (q, J=7.3 Hz, 2H), 0.94 (t, J=7.3 Hz, 2H).

Example 2
Preparation of 4-{{(phenoxycarbonyl)amino}-methyl}pyridine

To a solution of 4-(aminomethyl)pyridine (10.7 g, 98.5 mmol) in CH$_2$Cl$_2$ (245 mL) at 0°, was added Et$_3$N (14.2 mL, 19.9 g, 197 mmol) followed by dropwise addition of phenylchloroformate (14.8 mL, 18.5 g, 118 mmol). After stirring for 1 h, the resulting mixture was diluted with EtOAc (1.5 L), the organic phase was washed twice with water and brine, dried over sodium sulfate and concentrated under vacuum. Chromatography (SiO$_2$, gradient EtOAc to 10% MeOH/CHCl$_3$) gave a yellow solid which was recrystallized from EtOAc:hexane (2:1), to yield the desired compound (9.55 g, 41.85 mmol, 42% yield).

$^1$H NMR (400 MHz, CDCl$_3$) δ 8.61 (d, J=5.7 Hz, 2H), 7.40–7.15 (m, 7H), 5.61 (bs, 1H), 4.50 (d, J=6.4 Hz, 2H).

Example 3
Preparation of N-methyl-N-{[4-(trifluoromethyl)-phenyl]methyl}carbamoyl chloride To a solution of {4-(trifluoromethyl)phenyl}methyl bromide (20.0 g, 83.7 mmol) in EtOH was added MeNH$_2$ (100 mL of 40% aqueous solution, 1290 mmol). After 2 h the reaction was concentrated under vacuum. The aqueous phase was extracted with EtOAc (2×100 mL), The combined organic phase was washed with NaHCO$_3$ and brine, dried over magnesium sulfate, filtered and evaporated to dryness. The resulting residue was dissolved in HCl/dioxane (4N, 100 mL) and the solvent removed under vacuum. The resulting solid was triturated with Et$_2$O and collected by suction filtration to provide N-methyl {4-(trifluoromethyl)phenyl}methylamine hydrochloride salt (17.0 g, 90% yield) as a white solid.

The salt was suspended in CH$_2$Cl$_2$ (150 mL), cooled at 0° and DIEA was added (30.2 mL, 173 mmol) followed by a phosgene solution in toluene (1.93 M, 55 mL, 105.7 mmol). After 2 h at 0° the reaction mixture was concentrated. The resulting thick gum was extracted with Et$_2$O and evaporation of the extract gave a light yellow oil. This oil was further purified by flash chromatography (SiO$_2$, eluent 10% EtOAc in hexane) to give a pale yellow oil (16.0 g, 84% yield). $^1$H NMR (400 MHz, CDCl$_3$) δ 7.59 (m, 2H), 7.33 (m, 2H), 4.72 and 4.58 (2×s, 2H), 3.04 and 2.97 (2×s, 3H).

Example 4
Preparation of 2-oxo-4(R)-(pyrimidin-2-ylsulfanylmethyl) azetidine-1-carboxylic acid (1(R)-phenylpropyl)amide (Table 1, entry #104).

Step A

To a solution of 1-(tert-butyldimethylsilyl)-4-oxoazetidine-2(R)-carboxylic acid (15.0 g, 65.40 mmol) in THF (367 mL) at 0°, was added N-methylmorpholine (7.2 mL, 65.40 mmol) and isobutyl chloroformate (8.5 mL, 65.40 mmol). After stirring for 1.5 h at 0°, a solution of NaBH$_4$ (9.9 g, 261.61 mmol) in H$_2$O (98 mL) was added portion wise. The reaction was stirred 45 min, then diluted with EtOAc and quenched with aqueous HCl solution (10%) to pH 5–6. The organic phase was collected and the aqueous phase was extracted twice with EtOAc. The combined organic layers were washed with saturated aqueous NaHCO$_3$ and brine, dried (MgSO$_4$), filtered and concentrated. The residual oil was purified by flash chromatography (SiO$_2$, gradient 25% to 50% EtOAc/hexane) to provide 1-(tert-butyldimethylsilyl)-4(R)-(hydroxymethyl)azetidin-2-one (8.46 g, 60% yield) as a white solid. $^1$H NMR (400 MHz, CDCl$_3$) δ 3.74–3.69 (m, 1H), 3.65–3.56 (m, 2H), 3.1–2.98 (m, 1H), 2.81–2.76 (m, 1H), 2.01 (s, 1H), 0.89 (s, 9H), 0.18 (s, 3H), 0.16 (s, 3H). FAB MS m/z 216.2 (MH$^+$).

Step B

To a solution of 1-(tert-butyldimethylsilyl)-4(R)-(hydroxymethyl)azetidin-2-one (2.75 g, 12.77 mmol) in THF (80 mL) was added PPh$_3$ (6.70 g, 25.54 mmol). The reaction was cooled at 0° and DEAD (3.3 mL, 25.54 mmol) was added dropwise. After 5 min. 2-mercaptopyrimidine (3.60 g, 31.92 mmol) was added. After stirring for 15 min at 0° and 60 h at room temperature, the reaction mixture was concentrated. The residue was treated with EtOAc/hexane (1/1) and the resulting solid was filtered and rinsed with Et$_2$O. The filtrate was concentrated and purified by flash chromatography (SiO$_2$, 25% EtOAc/hexane) to provide 1-(tert-butyldimethylsilyl)-4(R)-(pyrimidin-2-ylsulfanylmethyl)azetidin-2-one (3.75 g, 95% yield) as clear oil. $^1$H NMR (400 MHz, CDCl$_3$) δ 8.70 (d, J=4.8 Hz, 2H), 7.20 (t, J=4.9 Hz, 1H), 4.08–4.01 (m, 2H), 3.41–3.36 (m, 1H), 3.99 (dd, J=14.3, 10.8 Hz, 1H), 2.98 (dd, J=15.6, 2.5 Hz, 1H), 1.18 (s, 9H), 0.53 (s, 3H), 0.49 (s, 3H).

Step C

To a solution of 1-(tert-butyldimethylsilyl)-4(R)-(pyrimidin-2-ylsulfanylmethyl)azetidin-2-one (280 mg, 0.905 mmol) in MeOH (4.5 mL) was added cesium fluoride (206 mg, 1.36 mmol). The reaction mixture was stirred 1.5 h at room temperature, then concentrated under vacuum. The residue was dissolved in CH$_2$Cl$_2$, washed with H$_2$O and brine, dried (MgSO$_4$), filtered and evaporated to give 4(R)-(pyrimidin-2-ylsulfanylmethyl)azetidin-2-one (184 mg) which was used as such. $^1$H NMR (400 MHz, CDCl$_3$) δ 8.52 (d, J=5.1 Hz, 2H), 7.02 (t, J=5.1 Hz, 1H), 6.13–5.93 (m,1H), 4.04–3.99 (m,1H), 3.54 (dd, J=14.0, 5.4 Hz, 1H), 3.27 (dd, J=14.0, 7.0, 1H), 3.14 (ddd, J=15.0, 5.1, 1.9 Hz, 1H), 2.78 (ddd, J=15.0, 2.2, 1.3 Hz, 1H).

Step D

To a solution of 4(R)-(pyrimidin-2-ylsulfanyl-methyl) azetidin-2-one (61.5 mg, 0.315 mmol) in THF (3 mL) at 0° was added dropwise LiHMDS (1M/THF) (0.33 mL, 0.331 mmol). After the reaction mixture was stirred 15 min at 0°, then cooled to −78°, 1(R)-phenylpropyl isocyanate (example 1) (0.53M/toluene, 0.63 mL, 0.315 mmol) was added dropwise and the mixture was warmed to room temperature and stirred for 1.5 h. The reaction mixture was quenched with $H_2O$ and diluted with EtOAc. The organic phase was washed with $H_2O$ and brine, dried ($MgSO_4$), filtered and evaporated. The product was purified by flash chromatography ($SiO_2$, 30% EtOAc/hexane) to give 2-oxo-4(R)-(pyrimidin-2-ylsulfanylmethyl)azetidine-1-carboxylic acid (1(R)-phenylpropyl)amide (75 mg, 67% yield) as a viscous gum. $^1H$ NMR (400 MHz, $CDCl_3$) δ 8.45 (d, J=4.8 Hz, 2H), 7.29–7.17 (m, 5H), 6.94 (t, J=4.8 Hz, 1H), 6.82 (d, J=8.3 Hz, 1H) 4.71 (q, J=7.6 Hz, 1H), 4.33–4.28 (m, 1H), 4.03 (dd, J=14.2, 3.3 Hz, 1H), 3.39 (dd, J=14.2, 8.3 Hz, 1H), 3.03 (dd, J=16.0, 5.6 Hz, 1H), 2.89 (dd, J=16.0, 3.0 Hz, 1H), 1.83–1.75 (m, 2H), 0.86 (t, J=7.3 Hz, 3H); IR (neat) υ 1758, 1692 $cm^{-1}$; FAB MS m/z 357.3 ($MH^+$); HRMS calcd. for $C_{18}H_{21}N_4O_2S$ ($MH^+$) 357.1385, found 357.1379.

Example 5

2-oxo-4(R)-[1(R)-(pyrimidin-2-ylsulfanyl)ethyl]azetidine-1-carboxylic acid (1(R)-phenylpropyl)amide and 2-oxo-4(R)-[1(S)-(pyrimidin-2-ylsulfanyl)ethyl]-azetidine-1-carboxylic acid (1(R)-phenylpropyl)amide (Table 2, mixture of entries #208 and 209).

To a solution of oxalyl chloride (0.31 mL, 3.58 mmol) in $CH_2Cl_2$ (22 mL) at −78° was added dropwise a solution of DMSO (0.48 mL, 6.83 mmol) in $CH_2Cl_2$ (1.4 mL). After 15 min, a solution of 1-(tert-butyldimethylsilyl)-4(R)-(hydroxymethyl)azetidin-2-one (700 mg, 3.25 mmol) in $CH_2Cl_2$ (3.3 mL) was added and the reaction was stirred an extra 45 min. Finally, DIEA (2.8 mL, 16.25 mmol) was added and the reaction was stirred at room temperature for 2 h. The resulting mixture was diluted with $H_2O$ and extracted with $CH_2Cl_2$. The organic phase was washed with aqueous HCl (10%), saturated $NaHCO_3$ and brine, dried ($MgSO_4$), filtered and concentrated. The crude aldehyde was immediately used in the next step. To the crude aldehyde dissolved in THF (29 mL) was added dropwise MeMgBr (3M/$Et_2O$, 2.7 mL, 8.18 mmol) The reaction mixture was stirred 1 h at 0° and 1 h at room temperature, followed by the addition of aqueous saturated $NH_4Cl$ solution. After extraction with EtOAc, the organic phase was washed with HCl (10%), saturated aqueous $NaHCO_3$ and brine, dried ($MgSO_4$), filtered and evaporated. The resulting mixture was purified by flash chromatography ($SiO_2$, 40% EtOAc-hexane) to give 1-(tert-butyldimethylsilyl)-4(R)-(1-hydroxyethyl)azetidin-2-one (580 mg, 77% yield for two steps) as a mixture of isomers. $^1H$ NMR (400 MHz, $CDCl_3$) δ 4.02–3.96 (m, 1H), 3.81 (q, J=6.5 Hz, 1H), 4.33–4.27 (m, 1H), 3.50–3.43 (m,2H), 3.01 (dd, J=15.6, 5.6 Hz, 1H), 2.95 (dd, J=15.3, 2.9 Hz, 1H), 2.84 (dd, J=15.1, 5.6 Hz, 1H), 2.58 (dd, J=15.6, 2.9 Hz, 1H), 1.14 (d, J=6.4 Hz, 3H), 1.07 (d, J=6.7 Hz, 3H), 0.92–0,91 (m, 18H), 0.22–0.11 (m, 6H)

The procedure of example 4, step B was followed to give 1-(tert-butyldimethylsilyl)-4(R)-[1-(pyrimidin-2-ylsulfanyl) ethyl]azetidin-2-one as a mixture of isomers. Separation of the two isomers was performed by preparative HPLC ($C_{18}$ column, 5% to 100% $CH_3CN/H_2O$/0.06% TFA).

Syn diastereoisomer (13.4 min): $^1H$ NMR (400 MHz, $CDCl_3$) δ 8.46 (d, J=4.8 Hz, 2H), 6.94 (t, J=4.8 Hz, 1H), 3.82 (q, J=3.0 Hz, 1H), 3.08 (dd, J=15.6, 5.7 Hz, 1H), 2.85 (dd, J=15.6, 2.9 Hz, 1H), 1.38 (d, J=6.7 Hz, 3H), 0.86 (s, 9H), 0.18 (s, 3H), 0.12 (s, 3H).

Anti diastereoisomer (15 min): $^1H$ NMR (400 MHz, $CDCl_3$) δ 8.46 (d, J=4.8 Hz, 2H), 6.96 (t, J=4.9 Hz, 1H), 4.26–4.21 (m, 1H), 4.07–4.02 (m, 1H), 2.98 (dd, J=15.7, 5.6 Hz, 1H), 2.81 (dd, J=14.6, 2.9 Hz, 1H), 1.31 (d, J=7.3 Hz, 3H), 0.94 (s, 9H), 0.32 (s, 3H), 0.24 (s, 3H).

The procedure of example 4, steps C and D was followed to give the desired compounds: 2-oxo-4(R)-[1(R)-(pyrimidin-2-ylsulfanyl)ethyl]azetidine-1-carboxylic acid (1(R)-phenylpropyl)amide. $^1H$ NMR (400 MHz, $CDCl_3$) δ 8.45 (d, J=4.8 Hz,2H), 7.29–7.18 (m, 5H), 6.93–6.89 (m, 2H), 4.76–4.66 (m, 2H), 4.53–4.49 (m, 1H), 3.00 (dd, J=16.2, 5.7 Hz, 1H), 2.90 (dd, J=16.3, 2.9 Hz, 1H), 1.86–1.79 (m, 2H), 1.37 (d, J=7.3 Hz, 3H), 0.88 (t, J=7.3 Hz, 3H); IR ($CHCl_3$) υ 1764, 1700 $cm^{-1}$; FAB MS m/z 371 ($MH^+$); HRMS calcd. for $C_{19}H_{23}N_4O_2S$: 371.1542 ($MH^+$); found: 371.1535. 2-oxo-4(R)-[1(S)-(pyrimidin-2-ylsulfanyl) ethyl]-azetidine-1-carboxylic acid (1(R)-phenylpropyl) amide. $^1H$ NMR (400 MHz, $CDCl_3$) δ 8.50 (d, J=4.8 Hz, 2H), 7.30–7.16 (m, 5H), 6.96 (t, J=4.8 Hz, 1H), 6.80 (d, J=8.6 Hz, 1H), 4.66–4.60 (m, 2H), 4.25–4.19 (m, 1H), 3.05 (dd, J=16.0, 5.6 Hz, 1H), 2.94 (dd, J=16.2, 2.6 Hz, 1H), 1.70 (q, J=7.3 Hz, 2H), 1.48 (d, J=7.0 Hz, 3H), 0.75 (t, J=7.5 Hz, 3H); IR (neat) υ 1764, 1702 $cm^{-1}$; FAB MS m/z 371 ($MH^+$); HRMS calcd. for $C_{19}H_{23}N_4O_2S$: 371.1542 ($MH^+$); found: 371.1535.

Example 6

Preparation of 2-oxo-4(R)-(phenylsulfanylmethyl) azetidine-1-carboxylic acid (pyridin-4-ylmethyl)amide (Table 2, entry #201).

Step A 1-(tert-Butyldimethylsilyl)-4(R)-(hydroxymethyl) azetidin-2-one (from example 4, step A) was deprotected using the same procedure as in example 4, step C, to give 4(R)-(hydroxymethyl)azetidin-2-one. $^1H$ NMR (400 MHz, $CDCl_3$) δ 6.86–6.67 (bs, 1H), 3.77 (dd, J=11.5, 3.4 Hz, 1H), 3.72–3.68 (m, 1H), 3.54 (dd, J=11.5, 6.0 Hz), 3.34–3.07 (bs, 1H), 2.91 (ddd, J=14.9, 5.1, 1.3 Hz, 1H), 2.66 (d, J=14.9 Hz, 1H).

To a solution of 4(R)-(hydroxymethyl)azetidin-2-one (502 mg, 4.96 mmol) in $CH_2Cl_2$ (7 mL) at 0° was added $Et_3N$ (0.83 mL, 5.96 mmol) followed by methanesulfonyl chloride (0.46 mL, 6.0 mmol) and stirred for 5 h at 0°. The reaction mixture was filtered and the filtrate concentrated in vacuo. The combined solids were purified by flash chromatography ($SiO_2$, 10% MeOH—$CHCl_3$) to yield the pure mesylate (610 mg, 3.40 mmol, 61% yield) as a white solid. $^1H$ NMR (400 MHz, $CDCl_3$) δ 6.07–5.90 (bs, 1H), 4.38 (dd, J=11.0, 3.7 Hz, 1H), 4.17 (dd, J=11.0, 7.2 Hz, 1H), 3.99–3.89 (m, 1H), 3.10 (ddd, J=15.2, 5.4, 2.0 Hz, 1H), 3.02 (s, 3H), 2.72 (ddd, J=15.2, 2.5, 1.3 Hz, 1H).

To a cold (0°) suspension of sodium hydride (54.0 mg, 2.24 mmol) in DMF (4 mL) was added thiophenol (223 mL, 2.17 mmol) and the reaction mixture was stirred at 0° for 1 h. The mesylate (300 mg, 1.67 mmol) was then added and stirring was continued at room temperature overnight. The reaction mixture was diluted with a 1:1 mixture of $Et_2O$/EtOAc (40 mL) and washed with $H_2O$, saturated aqueous $NaHCO_3$ and brine, dried ($MgSO_4$), filtered and concentrated. The residue was purified by flash chromatography ($SiO_2$, 70% EtOAc-hexane) to give 4(R)-(phenylsulfanylmethyl)azetidin-2-one (118 mg, 65% yield) as a colorless gum. $^1H$ NMR (400 MHz, $CDCl_3$) δ 7.38–7.31 (m, 2H), 7.29–7.15 (m, 3H), 5.97–5.80 (bs, 1H), 3.76–3.69 (m, 1H), 3.12 (dd, J=13.7, 5.1 Hz, 1H), 3.02 (ddd, J=15.0, 5.0, 1.9 Hz, 1H), 2.98 (dd, J=13.7, 7.6 Hz, 1H), 2.60 (ddd, J 15.0, 2.4, 1.5 Hz, 1H)

Step B

Following the same procedure as in example 4, step D, but using 4-(phenylsulfanylmethyl)azetidin-2-one and (pyridin-4-ylmethyl)carbamic acid phenyl ester as reactants gave 2-oxo-4(R)-(phenylsulfanylmethyl)azetidine-1-carboxylic acid (pyridin-4-ylmethyl)amide as a white solid.

$^1$H NMR (400 MHz, CDCl$_3$) δ 8.56–8.50 (m, 2H), 7.39–7.34 (m, 2H), 7.31–7.14 (m, 5H), 6.90–6.84 (m, 1H), 4.43 (dd, J=16.5, 6.4 Hz, 1H), 4.38 (dd, J=16.5, 6.4 Hz, 1H), 4.28–4.21 (m, 1H), 3.61 (dd, J=14.3, 2.9 Hz, 1H), 3.19 (dd, J=14.3, 7.9 Hz, 1H), 3.11 (dd, J=16.2, 5.7 Hz, 1H), 2.87 (dd, J=16.2, 2.9 Hz, 1H); IR (KBr) υ 3347, 1763, 1701 cm$^{-1}$; FAB MS m/z 328 (MH$^+$); HRMS calcd for C$_{17}$H$_{17}$N$_3$O$_2$S: 328.1119 (MH$^+$); found: 328.1129.

Example 7
Preparation of 4(R)-benzenesulfinylmethyl-2-oxoazetidine-1-carboxylic acid benzylamide (Table 2, entry #202).
Step A A solution of 4(R)-(phenylsulfanylmethyl)azetidin-2-one (from example 6, step A) (105 mg, 0.543 mmol) in MeOH (3 mL) was treated with an aqueous solution of oxone (167 mg, 0.272 mmol, 3 mL). After stirring at room temperature for 24 h, the reaction mixture was quenched with aqueous Na$_2$S$_2$O$_3$ (10%, 1 mL) and concentrated. The concentrate was diluted with EtOAc (5 mL) and brine (5 mL) and the two layers separated. The aqueous layer was re-extracted three times with CHCl$_3$ (20 mL) and the combined organic phases were dried (MgSO$_4$), filtered and concentrated. The residue was purified by flash chromatography (SiO$_2$, EtOAc) to afford 4(R)-(benzenesulfinylmethyl)azetidin-2-one (89.6 mg, 79% yield). $^1$H NMR (400 MHz, CDCl$_3$) δ (1:1 mixture of diastereoisomers) 7.61–7.45 (m, 10H), 6.29–6.14 (bs, 1H), 5.70–5.58 (bs, 1H), 4.16–4.08 (m, 1H), 3.88–3.80 (m, 1H), 3.27–3.05 (m, 4H), 2.92 (dd, J=13.3, 9.2 Hz, 1H), 2.90 (dd, J=13.3, 3.5 Hz, 1H), 2.75–2.67 (m, 1H), 2.66–2.58 (m, 1H).
Step B Following the same procedure as in example 4, step D, but using 4(R)-(benzenesulfinylmethyl)azetidin-2-one and benzylisocyanate as the starting material, gave 2(R)-benzenesulfinylmethyl-4-oxoazetidine-1-carboxylic acid benzyl amide.

$^1$H NMR (400 MHz, CDCl$_3$) δ (1:1 mixture of diastereoisomers) 7.62–7.55 (m, 4H), 7.54–7.45 (m, 6H), 7.31–7.24 (m, 4H), 7.24–7.17 (m, 6H), 6.85–6.70 (m, 2H), 4.57–4.49 (m, 1H), 4.43–4.30 (m, 4H), 4.18–4.11 (m, 1H), 3.66 (dd, J=13.0, 3.5 Hz, 1H), 3.51 (dd, J=13.7, 3.2 Hz, 1H), 3.33 (dd, J=16.5, 2.9 Hz, 1H), 3.25–3.16 (m, 1H), 3.24 (dd, J=16.0, 5.4 Hz, 1H), 3.20 (dd, J=13.7, 8.9 Hz, 1H), 3.06 (dd, J=16.5, 2.9 Hz, 1H), 2.89 (dd, J=13.0, 10.0 Hz, 1H); IR (KBr) υ 3325, 1774, 1691, 1036 cm$^{-1}$; FAB MS m/z 343 (MH$^+$); HRMS calcd. for C$_{18}$H$_{18}$N$_2$O$_3$S (MH$^+$) 343.1116, found: 343.1129.

Example 8
Preparation of 2(R)-benzenesulfonylmethyl-4-oxoazetidine-1-carboxylic acid benzyl amide (Table 2, entry #203).

Following the two step procedure as in example 7 but using an excess of aqueous oxone in step A, one obtained 4(R)-benzenesulfonylmethyl-2-oxoazetidine-1-carboxylic acid benzylamide as a white solid.

$^1$H NMR (400 MHz, CDCl$_3$) δ 7.90–7.84 (m, 2H), 7.67–7.61 (m, 1H), 7.58–7.51 (m, 2H), 7.30–7.16 (m, 5H), 6.74–6.66 (m, 1H), 4.38–4.25 (m, 3H), 4.14 (dd, J=14.0, 2.9 Hz, 1H), 3.22–3.17 (m, 3H); IR (KBr) υ 3328, 1779, 1693, 1303, 1150 cm$^{-1}$; FAB MS m/z 359 (MH$^+$); HRMS calcd. for C$_{18}$H$_{18}$N$_2$O$_4$S (MH$^+$) 359.1066, found: 359.1074.

Example 9
Preparation of 4(R)-(methylsulfanyl)methyl-2-oxoazetidine-1-carboxylic acid (1(R)-phenylpropyl)amide (Table 1, entry #127).

1-(tert-Butyldimethylsilyl)-4(R)-(hydroxymethyl)azetidin-2-one (from example 4, step A) (2.0 g, 9.29 mmol) was dissolved in CH$_2$Cl$_2$ (14 mL) and cooled to 0°. Et$_3$N (1.55 mL, 11.1 mmol) was added followed by 4-nitrobenzenesulfonyl chloride (2.47 g, 11.1 mmol) and stirred at 0° for 2 h. The reaction mixture was filtered and the filtrate concentrated in vacuo. Et$_2$O was added to the residue and the salt removed by filtration. The filtrate was concentrated and the crude product was purified by flash chromatography (SiO$_2$, 30% EtOAc-hexane) to yield the desired product as a yellow solid (2.98 g, 80% yield).

To a solution of the 4-nitrobenzenesulfonate derivative (1.0 g, 2.50 mmol) in MeCN (12 mL) was added potassium thioacetate (342 mg, 3.00 mmol). The reaction mixture was stirred at room temperature overnight and the orange suspension evaporated in vacuo. The residue was diluted with EtOAc (25 mL), washed with H$_2$O and brine, dried (MgSO$_4$) filtered and concentrated. The residue was purified by flash chromatography (SiO$_2$, 20% EtOAc-hexane) to give the thioacetate derivative (586 mg, 86% yield) as a yellow oil. $^1$H NMR (400 MHz, CDCl$_3$) δ 3.65–3.57 (m, 1H), 3.42 (dd, J=13.7, 3.2 Hz, 1H), 3.08 (dd, J=15.6, 5.4 Hz, 1H), 2.69 (dd, J=13.7, 9.2 Hz, 1H), 2.56 (dd, J=15.6, 2.7 Hz, 1H), 2.31 (s, 3H), 0.91 (s, 9H), 0.24 (s, 3H), 0.20 (s, 3H).

To a solution of the thioacetate (151 mg, 0.552 mmol) in MeOH (3 mL) was added a solution of LiOH (16.0 mg, 0.664 mmol) in MeOH (4 mL). The reaction mixture was stirred for 1 h at room temperature, MeI (41 mL, 0.659 mmol) was added and stirring was continued for 1 h. The reaction mixture was evaporated to dryness and purified by flash chromatography (SiO$_2$, 80% EtOAc-hexane) to yield 4(R)-(methylsulfanylmethyl)azetidin-2-one as a colorless oil (41.1 mg, 57% yield). $^1$H NMR (400 MHz, CDCl$_3$) δ 6.10–5.92 (bs, 1H), 3.79–3.72 (m, 1H), 3.06 (ddd, J=14.9, 5.0, 2.2 Hz, 1H), 2.73 (dd, J=13.6, 5.3 Hz, 1H), 2.66–2.59 (m, 1H), 2.58 (dd, J=13.6. 8.0 Hz, 1H), 2.10 (s, 3H)

Following the same procedure as in example 4, step D, but using 4(R)-(methylsulfanylmethyl)azetidin-2-one as starting material, gave 2(R)-(methylsulfanyl)methyl-4-oxoazetidine-1-carboxylic acid (1-phenylpropyl)amide as yellowish oil.

$^1$H NMR (400 MHz, CDCl$_3$) δ 7.31–7.24 (m, 2H), 7.23–7.16 (m, 3H), 6.83 (d, J=8.0 Hz, 1H), 4.68 (ddd, J=8.0, 7.6, 7.6 Hz, 1H), 4.18–4.10 (m, 1H), 3.14 (dd, J=14.0, 3.2 Hz, 1H), 3.08 (dd, J=16.0, 5.6 Hz, 1H), 2.83 (dd, J=16.0, 2.9 Hz, 1H), 2.77 (dd, J=14.0, 8.3 Hz, 1H), 2.10 (s, 3H), 1.83–1.73 (m, 2H), 0.85 (t, J=7.3 Hz, 3H); IR υ (CHCl$_3$) 1764, 1698 cm$^{-1}$; FAB MS m/z 293 (MH$^+$); HRMS calcd. for C$_{15}$H$_{20}$N$_2$O$_2$S (MH$^+$) 293.1324 found: 293.1311.

Example 10
Preparation of 2-oxo-4(R)-(piperidin-1-ylmethyl)azetidine-1-carboxylic acid (1(R)-phenylpropyl)amide (Table 2, entry #206).
Step A Iodine (4.25 g, 16.7 mmol) was added to a solution of 1-(tert-butyldimethylsilyl)-4(R)-(hydroxymethyl)azetidin-2-one (2.25 g, 10.47 mmol), Ph$_3$P (5.48 g, 20.93 mmol) and imidazole (1.64 g, 24.07 mmol) in MeCN (100 mL) at 0°. After stirring at room temperature for four days, the mixture was concentrated and suspended in EtOAc-hexane (1:1). The suspension was filtered through a silica gel pad and washed with EtOAc-hexane (1:1). Concentration of the filtrate and purification by flash chromatography (SiO$_2$, 10% EtOAc-hexane) afforded pure 1-(tert-butyldimethylsilyl)-4(R)-(iodomethyl)azetidin-2-one as a white solid (2.73 g, 80% yield). $^1$H NMR (400 MHz, CDCl$_3$) δ 3.72–3.66 (m, 1H), 3.50 (ddd, J=9.8, 3.2, 0.6 Hz, 1H), 3.21 (ddd, J=15.6, 5.4, 0.6 Hz, 1H), 3.11 (dd, J=9.8, 9.8 Hz, 1H), 2.76 (dd, J=15.6, 2.5 Hz, 1H), 0.96 (s, 9H), 0.27 (s, 3H), 0.22 (s, 3H).

Step B 1-(tert-butyldimethylsilyl)-4(R)-(iodomethyl)-azetidin-2-one (202 mg, 0.62 mmol) was heated at reflux in piperidine (5 mL) for 2 h. The solution was concentrated, dissolved in $CH_2Cl_2$ and washed with saturated $NaHCO_3$ and brine, dried ($MgSO_4$) and concentrated. The residue was purified by flash chromatography ($SiO_2$, EtOAc) to give 1-(tert-butyldimethylsilyl)-4(R)-(piperidin-1-ylmethyl)azetidin-2-one (116 mg, 71% yield). $^1$H NMR (400 MHz, $CDCl_3$) δ 3.70–3.63 (m, 1H), 3.16 (dd, J=15.3, 5.4 Hz, 1H), 2.70–2.61 (m, 2H), 2.45–2.26 (m, 5H), 1.60–1.53 (m, 4H), 1.46–1.38 (m, 2H), 0.96 (s, 9H), 0.24 (s, 6H).

Step C

Following the same procedures as in example 4, steps C and D one obtained 2-oxo-4(R)-(piperidin-1-ylmethyl)azetidine-1-carboxylic acid (1(R)-phenylpropyl)amide as a yellow gum.

$^1$H NMR (400 MHz, $CDCl_3$) δ 7.39–7.22 (m, 5H), 7.14–7.09 (m, 1H), 4.79 (q, J=7.6 Hz, 1H), 4.13–4.06 (m, 1H), 3.09 (dd, J=15.9, 5.7 Hz, 1H), 3.01 (dd, J=13.2, 3.5 Hz, 1H), 2.86 (dd, J=15.9, 2.5 Hz, 1H), 2.56 (dd, J=13.2, 7.6 Hz, 1H), 2.50–2.39 (m, 4H), 1.60–1.50 (m, 4H), 1.88–1.80 (m, 2H), 1.45–1.35 (m, 2H), 0.92 (t, 7.3 Hz, 3H); IR (neat) υ 3354, 1798, 1763, 1703; FAB MS m/z 330 (MH$^+$); HRMS calcd. For $C_{19}H_{28}N_3O_2$ (MH$^+$) 330.2181 found 330.2172.

Example 11

Preparation of 1-(2(R)-phenyl-pyrrolidine-1-carbonyl)-4-(pyrimidin-2-ylsulfanylmethyl)azetidin-2-one and 1-(2(S)-phenyl-pyrrolidine-1-carbonyl)-4-(pyrimidin-2-ylsulfanylmethyl)azetidin-2-one (Table 4, mixture of entries #402 and 403).

Step A

To a solution of 3-chloropropylamine hydrochloride (10 g, 77.0 mmol) and NaOH (10 N, 7.6 mL, 76 mmol) in THF (50 mL) was added di-tert-butyldicarbonate (15.9 g, 73 mmol) in THF (10 mL) followed by a mixture of MeOH/$H_2O$ (20/10 mL). The resulting solution was stirred for 2 h, then concentrated to approximately 15 mL and $Et_2O$ was added. The organic phase was washed twice with aqueous HCl (1.0 N), water and brine, dried ($MgSO_4$), filtered and concentrated to give N-Boc-3-chloropropylamine (14.2 g, 96% yield) as a yellow oil.

$^1$H-NMR (400 MHz, $CDCl_3$) δ 4.70 (m, 1H),3.59 (t, J=6.3 Hz, 2H),3.25 (m, 2H), 1.91 (m, 2H), 1.42 (s, 9H).

Step B

To a solution of N-Boc-3-chloropropylamine (10.0 g, 51.8 mmol) in THF was added sodium hydride (1.87 g, 78 mmol). After 20 min, benzyl bromide (9.24 mL, 78 mmol) was added and the reaction mixture was heated at reflux for 16 h. After cooling, the reaction mixture was diluted with $Et_2O$ (150 mL) and $H_2O$ (50 mL), the layers were separated and the aqueous layer was extracted twice with $Et_2O$. The combined organic phases were washed with $H_2O$ and brine, dried ($MgSO_4$), filtered and concentrated. The resulting yellow oil was purified by flash chromatography ($SiO_2$, 10% EtOAc-hexane) to give N-Boc-N-benzyl-3-chloropropylamine (1.97 g, 13% yield) as a pale yellow oil.

$^1$H-NMR (400 MHz, $CDCl_3$) δ 7.29–7.19 (m, 5H), 4.40 (bs, 2H), 3.45 (bm, 2H), 3.25 (bm, 2H), 1.90 (bm, 2H), 1.44, 1.39 (2s, 9H).

Step C

To a solution of tetramethylethylenediamine (0.83 mL, 5.47 mmol) and n-BuLi (1.6 M/hexane, 3.31 mL, 5.3 mmol) cooled at −78° was added dropwise N-Boc-N-benzyl-3-chloropropylamine (1.0 g, 3.53 mmol) in THF. The resulting yellow solution was stirred at −78° for 5 h. The reaction mixture was then quenched with aqueous $NH_4Cl$ (20 mL) and diluted with $Et_2O$ (150 mL), the layers were separated and the aqueous layer was extracted twice with $Et_2O$. The combined organic phases were washed with $H_2O$ and brine, dried ($MgSO_4$), filtered and concentrated. The resulting yellow oil was purified by flash chromatography ($SiO_2$, 10% EtOAc-hexane) to give 2-phenylpyrrolidine-1-carboxylic acid tert-butyl ester (0.57 g, 65% yield).

$^1$H-NMR (400 MHz, $CDCl_3$) δ 7.31–7.14 (m, 5H), 4.90–4.71 (m, 1H), 3.59 (m, 2H), 2.29 (m, 1H), 1.92–1.84 (m, 3H), 1.43, 1.16 (2s, 9H).

Step D

A solution of 2-phenylpyrrolidine-1-carboxylic acid tert-butyl ester (0.55 g, 2.23 mmol) in HCl/dioxane (4 M, 5 mL) was stirred for 30 min then evaporated to dryness. To the resulting oil was added $CH_2Cl_2$ (25 mL) and diisopropylethylamine (0.90 mL, 5.13 mmol), and the mixture was cooled to 0°. Phosgene (1.93 M in toluene, 1.62 mL, 3.12 mmol) was added rapidly, and the reaction mixture was stirred for 1 h then concentrated. The resulting solid was extracted with $Et_2O$, the undissolved residue was filtered and discarded. The ethereal solution was concentrated and the resulting oil was purified by flash chromatography ($SiO_2$, 10% EtOAc-hexane) to give 2-phenylpyrrolidine-1-carbamoyl chloride (0.43 g, 95% yield).

$^1$H-NMR (400 MHz, $CDCl_3$) δ 7.36–7.18 (m, 5H), 4.95–4.76 (m, 1H), 3.71 (m, 2H), 2.31 (m, 1H) 1.97–1.86 (m, 3H).

Step E

Following the same procedure as in example 4, step D using 4-(R)-(pyrimidin-2-ylsulfanylmethyl) azetidin-2-one and 2-phenylpyrrolidine-1-carbamoyl chloride as reactants gave the title compounds as a 1/1 mixture. Separation of the isomers was accomplished by flash chromatography ($SiO_2$, 50% EtOAc-hexane) to give isomer A (less polar, 0.047 g, 18% yield) and isomer B (more polar, 0.059 g, 31% yield). Isomer A (mixture of rotamers): $^1$H-NMR (400 MHz, $CDCl_3$) δ 8.44 (d, J=4.8 Hz, 2H), 7.27–7.06 (m, 5H), 6.94 (t, J=4.8 Hz, 1H), 5.50–4.80 (bm, 1H) 4.40– 3.50 (bm, 5H), 3.36 (m, 1H), 3.00–2.15 (bm, 3H), 1.95–1.72 (m, 3H); IR (neat) υ 1776, 1665; FAB MS m/z 369 (MH$^+$); HRMS calcd. for $C_{19}H_{21}O_2N_4S$: 369.1385 (MH$^+$); found: 369.1398.

Isomer B (mixture of rotamers): $^1$H-NMR (400 MHz, $CDCl_3$) δ 8.45 (bs, 2H), 7.25–7.16 (m, 5H), 6.94 (bm, 1H), 5.49 and 4.99 (2 bm, 1H), 4.44–3.45 (bm, 4H), 3.11–2.76 (bm, 2H), 2.44–2.29 (bm, 1H), 2.18–1.10 (bm, 4H); IR (neat) υ 1776, 1665; FAB MS m/z 369 (MH$^+$); HRMS calcd. for $C_{19}H_{21}O_2N_4S$: 369.1385 (MH$^+$); found: 369.1402.

Example 12

Anti-herpes Activity

The following two assays (A and B) were used to evaluate anti HCMV activity.

1. HCMV $N_O$ Protease Assay

Material & Methods: Fluorescence measurements were recorded on a Perkin-Elmer LS-50B spectrofluorimeter equipped with a plate reader accessory. UV measurements were recorded on a Thermomax® microplate reader from Molecular Devices Corporation, Menlo Park, Calif., USA.

HCMV $N_O$ protease was assayed with an internally quenched fluorogenic substrate based on the maturation cleavage site (Abz-VVNASSRLY(3-$NO_2$)R—OH, $k_{cat}/K_M$=260 $M^{-1}s^{-1}$). The fluorescence increase upon cleavage of the Ala-Ser amide bond was monitored using excitation λ=312 nm (slit 2.5 nm) and emission λ=415 nm (slit 5 nm). A protocol adaptable to a 96-well plate format was designed for the determination of $IC_{50}$ values of inhibitors.

Briefly, HCMV $N_O$ was incubated for 2.5 h at 30° in the presence of the substrate with a range of sequentially diluted inhibitor concentrations (300 to 0.06 µM depending on the potency of each compound). After this period, enzymatic hydrolysis of the fluorogenic substrate in the absence of inhibitor led to about a 30% conversion. Quenching was not required before fluorescence measurement since the total scanning time by the plate reader accessory was brief relative to the duration of the reaction. The aqueous incubation buffer contained 50 mM tris(hydroxymethyl) aminomethane.HCl pH 8, 0.5M $Na_2SO_4$, 50 mM NaCl, 0.1 mM EDTA, 1 mM tris(2-carboxyethyl)phosphine.HCl, 3% v/v DMSO and 0.05% w/v casein. The final concentrations of HCMV $N_O$ protease (expressed in terms of total monomer concentration) and substrate were 100 nM and 5 µM respectively. $IC_{50}$ values were obtained through fitting of the inhibition curve to a competitive inhibition model using SAS NLIN procedure. The mode of inhibition was determined by measurements of the initial rates (in cuvettes) at various substrate concentrations in the buffer as described above. The $IC_{50}$ values listed in the following tables were obtained according to this assay.

B. Plaque Reduction Assay (PRA):

Hs-68 cells (ATCC # CRL 1635) were seeded in 12-well plates at 83,000 cells/well in 1 mL of DMEM medium (Gibco Canada Inc.) supplemented with 10% fetal bovine serum (FBS, Gibco Canada Inc.). The plates were incubated for 3 days at 37° to allow the cells to reach 80–90% confluency prior to the assay.

The medium was removed from the cells by aspiration. The cells were then infected with approximately 50 PFU of HCMV (strain AD169, ATCC VR-538) in DMEM medium supplemented with 5% inactivated FBS (assay medium). (DMEM medium is commercially available and has been described by R. Dulbecco et al., *Virology* 1959, 8, 396.) The virus was allowed to adsorb to cells for 2 h at 37°. Following viral adsorption, the medium was removed from the wells by aspiration. The cells were then incubated with or without 1 mL of appropriate concentrations of test reagent in assay medium. Occasionally, test compounds were added 24 h post-infection. After 4 days of incubation at 37°, the medium was exchanged with fresh medium containing test compound and 4 days later the cells were fixed with 1% aqueous formaldehyde and stained with a 2% violet solution in 20% ethanol in water. Microscopic plaques were counted using a stereomicroscope. Drug effects were calculated as a percent reduction in the number of plaques in the presence of each drug concentration compared to the number observed in the absence of drug. Ganciclovir was used as a positive control in all experiments.

The $EC_{50}$ values obtained according to this assay for certain azetidine derivatives of this invention are listed in the following table under the heading $EC_{50}$.

Example 13

In conjunction with the appropriate starting materials and intermediates, the procedures of examples 1 to 11 can be used to prepare other compounds of formula 1. Examples of compounds thus prepared are listed in the following Tables 1, 2, 3 and 4 together with mass spectrum data for the compounds, and results from the assays A and B of example 12.

Cytotoxic effects noted as $TC_{50}$ in the following tables were determined according to the tetrazolium salt (MTT) metabolic assay, F. Denizot and F. Lang, *J. Immun. Meth.*, 1986, 89, 271.

Symbols used in the following tables includes Ph: phenyl; Bn: benzyl; Py: pyridinyl; $CF_3$: trifluoromethyl; MS: FAB mass spectrometry unless otherwise noted (such as ES). mixture was diluted with $Et_2O$ (150 mL) and $H_2O$ (50 mL), the layers were separated and the aqueous layer was extracted twice with $Et_2O$. The combined organic phases were washed with $H_2O$ and brine, dried ($MgSO_4$), filtered and concentrated. The resulting yellow oil was purified by flash chromatography ($SiO_2$, 10% EtOAc-hexane) to give N-Boc-N-benzyl-3-chloropropylamine (1.97 g, 13% yield) as a pale yellow oil.

$^1$H-NMR (400 MHz, $CDCl_3$) δ 7.29–7.19 (m, 5H), 4.40 (bs, 2H), 3.45 (bm, 2H), 3.25 (bm, 2H), 1.90 (bm, 2H), 1.44, 1.39 (2s, 9H).

Step C

To a solution of tetramethylethylenediamine (0.83 mL, 5.47 mmol) and n-BuLi (1.6 M/hexane, 3.31 mL, 5.3 mmol) cooled at −78° was added dropwise N-Boc-N-benzyl-3-chloropropylamine (1.0 g, 3.53 mmol) in THF. The resulting yellow solution was stirred at −78° for 5 h. The reaction mixture was then quenched with aqueous $NH_4Cl$ (20 mL) and diluted with $Et_2O$ (150 mL), the layers were separated and the aqueous layer was extracted twice with $Et_2O$. The combined organic phases were washed with $H_2O$ and brine, dried ($MgSO_4$), filtered and concentrated. The resulting yellow oil was purified by flash chromatography ($SiO_2$, 10% EtOAc-hexane) to give 2-phenylpyrrolidine-1-carboxylic acid tert-butyl ester (0.57 g, 65% yield).

TABLE 1

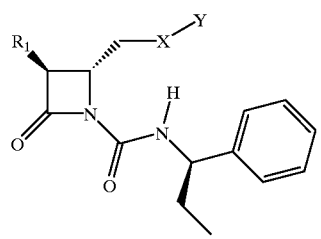

| entry # | $R_1$ | X | Y | $IC_{50}$ µM | $EC_{50}$ µM | $TC_{50}$ µM | MS $(M + H)^+$ |
|---|---|---|---|---|---|---|---|
| 101 | H | O | 2-pyridinyl | 8.4 | 55 | 151 | 340.2 |
| 102 | Me | O | phenyl | 2.7 | >250 | >250 | 353.2 |
| 103 | H | S | 2-pyridinyl | 4.0 | 150 | >250 | 356.1 |

TABLE 1-continued

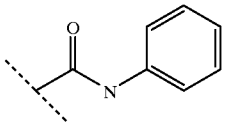

| entry # | R₁ | X | Y | IC$_{50}$ μM | EC$_{50}$ μM | TC$_{50}$ μM | MS (M + H)⁺ |
|---|---|---|---|---|---|---|---|
| 104 | H | S | 2-pyrimidinyl | 2.8 | 120 | >209 | 357.3 |
| 105 | H | S | 4,6-Me₂-2-pyrimidinyl | 4.6 | 88 | >250 | 385.3 |
| 106 | H | S | 2-benzothiazolyl | 3.3 | >250 | >250 | 412.3 |
| 107 | H | S | 4-pyridinyl | 2.0 | 92 | >233 | 356 |
| 108 | Me | S | 2-pyridinyl | 1.2 | 180 | >250 | 370.2 |
| 109 | Me | S | 2-benzothiazolyl | 1.2 | 160 | >250 | 426.2 |
| 110 | Me | S | isopropyl | 5.6 | | | 335 |
| 111 | Me | S | 2-pyrimidinyl | 0.65 | 110 | >250 | 371.2 |
| 112 | Me | S | 2-bensoxazolyl | 0.94 | 140 | >250 | 410.2 |
| 113 | Me | S | phenyl | 1.6 | | | 369 |
| 114 | Me | S | cyclohexyl | 3.0 | >250 | >250 | 375 |
| 115 | Me | S | 2-Me-3-furanyl | 4.2 | 85 | >250 | 373.1 |
| 116 | Me | S | N-Me-2-imidazolyl | 1.9 | 130 | >250 | 373 |
| 117 | Me | S | 2-Me-propyl | 3.5 | 110 | >250 | 349 |
| 118 | Me | S | 4-pyridinyl | 1.6 | 55 | 199 | 370.1 |
| 119 | Me | S | 1-Me-5-tetrazolyl | 1.4 | 80 | >250 | 375.1 |
| 120 | Me | S | ethyl | 4.0 | | | 321 |
| 121 | Me | S | cyclopentyl | 4.3 | 150 | >250 | 361 |
| 122 | Me | S | 4-OMe-phenyl | 4.8 | >250 | >250 | 399.2 |
| 123 | Me | S | 4-Me-2-pyrimidinyl | 0.98 | 150 | >250 | 385.1 |
| 124 | H | S | 4-Me-2-pyrimidinyl | 4.0 | >250 | >250 | 371 |
| 125 | Me | S | 2-thiazolo[4,5-b]pyridinyl | 1.1 | 140 | >250 | 427 |
| 126 | Me | S | 4,6-Me₂-2-pyrimidinyl | 2.8 | 25 | >63 | 399.2 |
| 127 | H | S | Methyl | 3.8 | >250 | >250 | 293 |
| 128 | H | S | 2,2-Me₂-propyl | 4.7 | >250 | >250 | 363 |
| 129 | H | S | Phenyl | 2.5 | >250 | >250 | 355.2 |
| 130 | H | O | Phenyl | 5.2 | 101 | >250 | 339.1 |
| 131 | H | O | 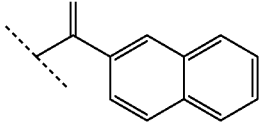 | 1.4 | 20 | >32 | 382 |
| 132 | H | O | methoxy | 3 | 210 | >250 | 305 |
| 133 | H | O | 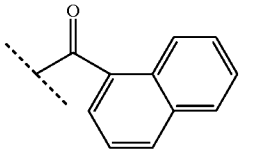 | 0.95 | 18 | >26 | 417 |
| 134 | H | O | 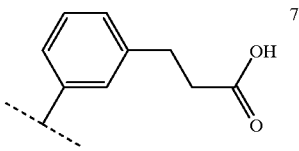 | 1.46 | 9 | >13 | 417 |
| 135 | H | O |  | 7.1 | | | 411 |

TABLE 1-continued
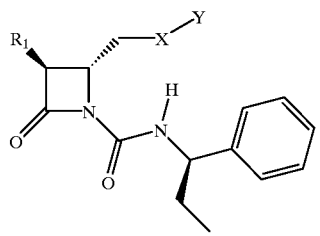
| entry # | R₁ | X | Y | IC$_{50}$ μM | EC$_{50}$ μM | TC$_{50}$ μM | MS (M + H)⁺ |
|---|---|---|---|---|---|---|---|
| 136 | H | O | *3-(CH₂COOH)phenyl* | 9.1 | | | 397.1 |
| 137 | H | N(Me) | Bn | 9.9 | >147 | >147 | 366.2 |
| 138 | H | S | *4-(NHC(O)CH=CH₂)phenyl* | 5 | | | 424.2 |
| 139 | H | S | *thiazolo[5,4-b]pyridin-2-yl* | 2.8 | >53 | >53 | 413.2 (ES) |
| 140 | H | S | *1-methylimidazol-2-yl* | 3.7 | >268 | >268 | 359.2 (ES) |
| 141 | H | S | *benzoxazol-2-yl* | 3.8 | 22 | >26 | 396.1 |
| 142 | H | S | *pyrimidin-2-yl* | 13 | | | 371 |
| 143 | H | SO | *pyrimidin-2-yl* | 1.4 | 59 | >253 | 369 |
| 144 | H | SO₂ | Ph | 1.9 | 5 | 58 | 385 |

TABLE 1-continued

| entry # | R₁ | X | Y | IC$_{50}$ μM | EC$_{50}$ μM | TC$_{50}$ μM | MS (M + H)⁺ |
|---|---|---|---|---|---|---|---|
| 145 | H | O | (acetylphenyl) | 1.12 | 250 | 250 | |

TABLE 2

| entry # | R₂ | R₁₀ | R₁₁ | X | Y | IC$_{50}$ μM | EC$_{50}$ μM | TC$_{50}$ μM | MS (M + H)⁺ |
|---|---|---|---|---|---|---|---|---|---|
| 201 | H | H | 4-Py | S | phenyl | 7.9 | 75 | >270 | 328 |
| 202 | H | H | Ph | SO | phenyl | 13 | | | 343 |
| 203 | H | H | Ph | SO₂ | phenyl | 24 | | | 359 |
| 204 | H | H | Ph | NH | CO-phenyl | 2.6 | 120 | >250 | 338 |
| 205 | H | (R)Et | Ph | N* | morpholinyl | 9.4 | | | 332 |
| 206 | H | (R)Et | Ph | N** | piperidinyl | 3.7 | >250 | >250 | 330 |
| 207 | H | H | Py | O | acetyl | 46 | | | 278.1 |
| 208 | (S)Me | (R)Et | Ph | S | pyrimidinyl | 4.5 | >250 | >250 | 371.2 |
| 209 | (R)Me | (R)Et | Ph | S | pyrimidinyl | 3.4 | 80 | >168 | 371 |
| 210 | H | (R)Et | Ph | N | diethyl | 48 | | | 318 |
| 211 | H | (methylindanyl) | | S | (methyltetrazolyl) | 7.9 | 140 | 188 | 359 |
| 212 | H | (R)Me | Ph | S | Ph | 4.4 | 31 | >52 | 341 |
| 213 | H | (S)Et | Ph | S | pyrimidinyl | 17 | | | 357 |
| 214 | H | H | Bn | S | pyrimidinyl | 24 | | | 329 |

*N included in morpholino ring; **N included in piperidino ring.

TABLE 3

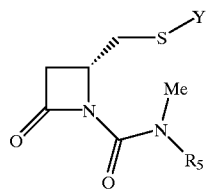

| entry # | R5 | Y | IC50 μM | EC50 μM | TC50 μM | MS (M + H)+ |
|---|---|---|---|---|---|---|
| 301 | 4-CF3-Bn | 2-pyrimidinyl | 1.7 | 95 | >250 | 411 |
| 302 | 4-(CO2Me)-Bn | 2-pyrimidinyl | 3.9 | 170 | >250 | 401 |
| 303 | CH2-2-Furanyl | 2-pyrimidinyl | 17 | | | 333.3 |
| 304 | 4-(CO2Bn)-Bn | 2-pyrimidinyl | 2.5 | 120 | >250 | 477.2 |
| 305 | 4-(CO)(Nme2)-Bn | 2-pyrimidinyl | 14 | 210 | >250 | 414 |
| 306 | Ph | 2-pyrimidinyl | 22 | | | 329 |
| 307 | 4-(CO2Me)-Bn | 4-Me-2-pyrimidinyl | 3.5 | 105 | >250 | 415.2 |
| 308 | 4-(CO2Me)-Bn | N-Me-2-imidazolyl | 22 | | | 403.2 |
| 309 | 4-(CO2Me)-Bn | 1-Me-5-tetrazolyl | 1.0 | 130 | >250 | 405.2 |
| 310 | 4-(CO2Me)-Bn | 2-benzoxazolyl | 3.3 | | | 440 |
| 311 | 4-CF3-Bn | 4-pyridinyl | 0.6 | 250 | >250 | 410 |
| 312 | 4-CN-Bn | 2-pyrimidinyl | 4.7 | 100 | | 368.1 |
| 313 | 4-F-Bn | 2-pyrimidinyl | 8.3 | 110 | >250 | 361.1 |
| 314 | 4-CF3-Bn | N-Me-2-imidazolyl | 5.5 | >250 | >250 | 413.1 |
| 315 | CH2-2-pyranyl | 2-pyrimidinyl | 28 | | | 351.1 |
| 316 | 4-CF3-Bn | 2-thiazolo[4,5-b]pyridinyl | 1.6 | 14 | >18 | 467 |
| 317 | 3,4-CH2—O2-Bn | 2-pyrimidinyl | 9 | 140 | >249 | 387 |
| 318 | Bn | 2-pyrimidinyl | 10 | 150 | >150 | 343 |

TABLE 3-continued

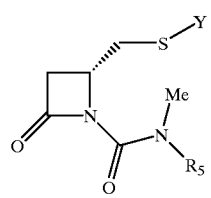

| entry # | R5 | Y | IC50 μM | EC50 μM | TC50 μM | MS (M + H)+ |
|---|---|---|---|---|---|---|
| 319 | 4-CF3-Bn | 2-benzoxazolyl | 1.7 | 160 | >250 | 450 |
| 320 | 4-CF3-Bn | 1-Me-5-tetrazolyl | 0.47 | 69 | >250 | 415 |
| 321 | CH[(S)Et]Ph | | 21 | | | 371 |

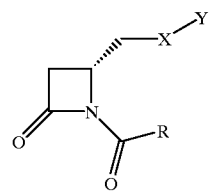

| entry # | R5 | Y | IC50 μM | EC50 μM | TC50 μM | MS (M + H)+ |
|---|---|---|---|---|---|---|
| 322 | 4-nitrobenzyl | 2-pyrimidinyl | 1.2 | >118 | >118 | 388.1 |

TABLE 4

| entry # | R | X | Y | IC50 μM | EC50 μM | TC50 μM | FAB/MS (M + H)+ |
|---|---|---|---|---|---|---|---|
| 401 | 2-CO2Bn-1-pyrrolidinyl | S | 2-pyrimidinyl | 21 | | | 427.1 |
| 402 | 2-(S)-Ph-1-pyrrolidinyl | S | 2-pyrimidinyl | 34 | | | 369.1 |
| 403 | 2-(R)-Ph-1-pyrrolidinyl | S | 2-pyrimidinyl | 14 | 95 | >250 | 369 |
| 404 | 3-phenyl-1-pyrrolidinyl | S | 2-pyrimidinyl | 18.5 | | | 369 |
| 405 | 3-phenyl-1-pyrrolidinyl | S | 2-pyrimidinyl | 35.5 | | | 369 |

TABLE 4-continued

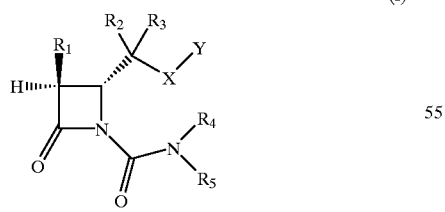

| entry # | R | X | Y | IC$_{50}$ µM | EC$_{50}$ µM | TC$_{50}$ µM | FAB/MS (M + H)$^+$ |
|---|---|---|---|---|---|---|---|
| 406 | [piperidine-N-(benzyl ester)] | S | [pyrimidin-2-yl] | 45 | | | 441 |
| 407 | [2-(4-nitrophenyl)pyrrolidin-1-yl] | S | [1-methyltetrazol-5-yl] | 0.8 | 250 | >250 | 274 |
| 408 | [2-(2-nitrophenyl)pyrrolidin-1-yl] | S | [1-methyltetrazol-5-yl] | 3.6 | 100 | >133 | 418 |

Conclusion

From the results presented in tables 1 to 4, it can be concluded that the compounds of formula 1 are active against the protease of the HCMV virus. In addition, several of these compounds also inhibit virus replication in virus-infected cells, thereby indicating that these compounds are active in vivo in mammals, particularly humans.

The TC$_{50}$ reported in tables 1 to 4 also indicate that these compounds are non-toxic and have a therapeutic window that allows safe use of these compounds in mammals, including humans.

What is claimed is:

1. A compound of formula 1:

(I)

wherein R$_1$ is hydrogen, methyl, ethyl, methoxy or methylthio;
R$_2$ and R$_3$ each independently are hydrogen or C$_{1-3}$ alkyl;
R$_4$ is hydrogen, lower alkyl, methoxy, ethoxy, or benzyloxy;
R$_5$ is lower alkyl, lower cycloalkyl, (CH$_2$)$_m$C(O)OR$_6$ wherein m is the integer 1 or 2 and R$_6$ is lower alkyl or phenyl(lower alkyl);
phenyl, phenyl monosubstituted, disubstituted or trisubstituted with a substituent selected independently from the group consisting of lower alkyl, lower alkoxy, lower alkylthio, halo, hydroxy and amino; phenyl (lower alkyl), phenyl(lower alkyl) monosubstituted or disubstituted on the phenyl portion thereof with a substituent selected independently from the group consisting of lower alkyl, lower alkoxy, lower alkylthio, halo, hydroxy, nitro, amino, lower alkylamino, di(lower alkyl)amino, lower alkylamido, di(lower alkyl) aminocarbonyl, cyano, trifluoromethyl, (trifluoromethyl)thio, (trifluoromethyl)sulfinyl, (trifluoromethyl)sulfonyl and C(O)OR$_7$ wherein R$_7$ is lower alkyl or phenyl(lower alkyl);
Het or Het (lower alkyl) wherein Het represents a monovalent five or six membered saturated or unsaturated heterocycle containing from one or four heteroatoms selected from N, O or S, said Het being optionally mono- or di-substituted with lower alkyl, lower alkoxy, halo or hydroxy;
5-(benzo[1,3]dioxolyl)methyl, (1(R)-1-naphthalenyl) ethyl, 2-benzothiazolyl or 2-thiazolo[4,5-b]pyridinyl; or
R$_4$ and R$_5$ together with the nitrogen atom to which they are attached form a piperidino, morpholino, thiomorpholino, piperazino, N-methylpiperazino, 1-(3, 4-dihydro-1H-isoquinolinyl) or 2-(3,4-dihydro-1H-isoquinolinyl) or a pyrrolidino ring optionally substituted with benzyloxycarbonyl or with phenyl, said phenyl ring optionally mono- or di-substituted with a substituent selected independently from the group consisting of lower alkyl, lower alkoxy, lower alkylthio, halo, hydroxy, nitro, amino, lower alkylamino, di(lower alkyl)amino, lower alkylamido, di(lower alkyl)aminocarbonyl, cyano, trifluoromethyl, (trifluoromethyl)thio, (trifluoromethyl)sulfinyl, (trifluoromethyl)sulfonyl and $C(O)OR_7$ wherein $R_7$ is as defined above;

X is selected from the group consisting of O, S, SO, $SO_2$, $NR_8$, wherein $R_8$ is H or lower alkyl; and Y is $C_{1-10}$ alkyl or $C_{3-10}$ cycloalkyl;

$(CH_2)_{0-1}$phenyl, said phenyl ring optionally mono- or di-substituted with a lower alkyl or lower alkoxy, said phenyl ring being optionally fused with an aromatic ring to form a bicyclic ring, said aromatic ring optionally containing a heteroatom selected from the group consisting of N, O and S;

Het or Het (lower alkyl) wherein Het is as defined above, said Het being optionally mono- or di-substituted with lower alkyl or lower alkoxy group; and optionally fused with an aromatic ring to form a bicyclic ring, said aromatic ring optionally containing one or more heteroatoms selected from the group consisting of N, O and S; and $C(O)R_9$ wherein $R_9$ is lower alkyl, or phenyl (lower alkyl);

or when X is $NR_8$, wherein $R_8$ is lower alkyl and Y is lower alkyl or lower alkoxy, X and Y are joined together to form a morpholino or piperidino ring;

or a therapeutically acceptable acid addition salt thereof.

2. The compound according to claim 1 wherein $R_1$ is hydrogen or $C_{1-2}$ alkyl;

$R_2$ and $R_3$ each independently are hydrogen, methyl or ethyl;

$R_4$ is hydrogen or lower alkyl;

$R_5$ is phenyl optionally substituted with a substituent selected independently from the group consisting of lower alkyl, lower alkoxy;

phenyl(lower alkyl) optionally mono- or di-substituted on the phenyl portion thereof with a substituent selected independently from the group consisting of lower alkyl, lower alkoxy, nitro, halo, cyano, trifluoromethyl, and $C(O)OR_7$ wherein $R_7$ is lower alkyl or phenyl(lower alkyl);

Het (lower alkyl), wherein Het is as defined in claim 1;

or $R_4$ and $R_5$ together with the nitrogen atom to which they are attached form a pyrrolidino optionally substituted with benzyloxycarbonyl or phenyl, said phenyl ring optionally mono- or di-substituted with halo, nitro, cyano or trifluoromethyl;

X is selected from the group consisting of O, S, $NR_8$, wherein $R_8$ is H or lower alkyl; and Y is $C_{1-10}$ alkyl or $C_{3-10}$ cycloalkyl; phenyl or benzyl optionally mono- or di-substituted with lower alkyl or lower alkoxy, said phenyl ring being optionally fused with an aromatic ring to form a bicyclic ring, said aromatic ring optionally containing a heteroatom selected from the group consisting of N, O and S; and Het or $CH_2$-Het wherein Het is as defined in claim 1;

or when X is $NR_8$, wherein $R_8$ is lower alkyl and Y is lower alkyl, X and Y are joined together to form a piperidino ring.

3. The compound according to claim 2 wherein $R_1$, $R_2$ and $R_3$ each independently is hydrogen, methyl or ethyl;

$R_4$ is hydrogen or $C_{1-3}$ alkyl;

$R_5$ is phenyl optionally substituted with a substituent selected independently from the group consisting of lower alkyl or lower alkoxy;

($C_{1-2}$ alkyl)phenyl optionally mono- or di-substituted on the phenyl portion thereof with a substituent selected independently from the group consisting of lower alkyl, lower alkoxy, nitro, halo, cyano, trifluoromethyl, and $C(O)OR_7$ wherein $R_7$ is lower alkyl or (lower alkyl) phenyl;

X is selected from the group consisting of O, S, $NR_8$, wherein $R_8$ is H or lower alkyl; and Y is $C_{1-10}$ alkyl or $C_{3-10}$ cycloalkyl; phenyl optionally mono- or di-substituted with lower alkyl or lower alkoxy; or Het wherein Het is as defined in claim 2;

or when X is $NR_8$, wherein $R_8$ is lower alkyl and Y is lower alkyl, X and Y are joined together to form a piperidino ring.

4. The compound according to claim 3 wherein $R_1$, $R_2$ and $R_3$ each independently is hydrogen;

$R_4$ is hydrogen or methyl;

$R_5$ is benzyl optionally mono-substituted on the phenyl portion thereof with nitro or trifluromethyl, or 1(R)-phenylethyl;

X is S; and

Y is pyrimidine optionally substituted with lower alkyl; pyridine; N-Me-tetrazole; or benzoxazole.

5. A pharmaceutical composition for treating cytomegalovirus infections in a mammal, including human, comprising a compound of formula 1 according to claim 1, or a therapeutically acceptable salt thereof, and a pharmaceutically acceptable carrier.

6. A method for treating cytomegalovirus infections in a mammal, including human, comprising administering thereto an effective amount of the compound of formula 1 according to claim 1, or a therapeutically acceptable salt thereof.

7. A method for protecting human cells against cytomegalovirus pathogenesis comprising treating said cells with an anti-cytomegalovirus effective amount of a compound of formula 1 according to claim 1, or a therapeutically acceptable salt thereof.

8. The compound of formula 1 according to claim 1 in combination with anti-herpes compound, selected from the group consisting of ganciclovir, foscarnet, acyclovir, valaciclovir, famciclovir, cidofovir, penciclovir and lobucavir.

9. The compound of formula 1 according to claim 1 in combination with anti-retroviral compound selected from the group consisting of reverse transcriptase inhibitors and protease inhibitors.

* * * * *